United States Patent
Bilan

(10) Patent No.: US 8,396,228 B2
(45) Date of Patent: Mar. 12, 2013

(54) FLOATING BALLAST MASS ACTIVE STETHOSCOPE OR SOUND PICKUP DEVICE

(75) Inventor: Frank Albert Bilan, Newman, CA (US)

(73) Assignee: Stethoscope Technologies, Inc., San Jose, CA (US)

( * ) Notice: Subject to any disclaimer, the term of this patent is extended or adjusted under 35 U.S.C. 154(b) by 1022 days.

(21) Appl. No.: 12/038,142

(22) Filed: Feb. 27, 2008

(65) Prior Publication Data

US 2009/0211838 A1    Aug. 27, 2009

(51) Int. Cl.
*A61B 7/04* (2006.01)
*A61B 7/02* (2006.01)

(52) U.S. Cl. .......................... 381/67; 181/131
(58) Field of Classification Search ............... 381/67, 381/66, 61; 181/131
See application file for complete search history.

(56) References Cited

U.S. PATENT DOCUMENTS

| | | | | |
|---|---|---|---|---|
| 3,233,041 A * | 2/1966 | Croslin | ........................... | 381/67 |
| 3,555,187 A * | 1/1971 | Rowley | ......................... | 600/528 |
| 4,235,113 A * | 11/1980 | Carome | ........................ | 73/655 |
| 4,270,627 A | 6/1981 | Hill | ............................... | 181/131 |
| 4,878,501 A | 11/1989 | Shue | .............................. | 128/715 |
| 5,022,405 A | 6/1991 | Hok et al. | ....................... | 128/715 |
| 5,027,825 A | 7/1991 | Phelps et al. | ................... | 128/715 |
| 5,335,210 A * | 8/1994 | Bernstein | ...................... | 367/163 |
| 5,539,831 A * | 7/1996 | Harley | .............................. | 381/67 |
| 5,825,895 A | 10/1998 | Grasfield et al. | ................. | 381/67 |
| 6,498,854 B1 | 12/2002 | Smith | .............................. | 381/67 |
| 6,523,639 B1 | 2/2003 | Shieh | ............................. | 181/131 |
| 6,587,564 B1 * | 7/2003 | Cusson | ............................ | 381/67 |
| 6,661,897 B2 | 12/2003 | Smith | .............................. | 381/67 |
| 6,852,084 B1 * | 2/2005 | Boesen | ......................... | 600/528 |
| 7,082,202 B1 | 7/2006 | Orten | .............................. | 381/67 |
| 2003/0201138 A1 | 10/2003 | Drummond | ................... | 181/131 |
| 2005/0058298 A1 * | 3/2005 | Smith | .............................. | 381/67 |
| 2006/0285696 A1 | 12/2006 | Houtsma | .......................... | 381/67 |
| 2007/0113654 A1 * | 5/2007 | Carim et al. | .................... | 73/578 |
| 2007/0165872 A1 | 7/2007 | Bridger et al. | .................. | 381/67 |
| 2007/0278033 A1 * | 12/2007 | Bank et al. | ..................... | 181/161 |

* cited by examiner

*Primary Examiner* — Matthew Landau
*Assistant Examiner* — Khaja Ahmad
(74) *Attorney, Agent, or Firm* — Girard & Equitz LLP

(57) ABSTRACT

An active stethoscope or other sound detection device, including a diaphragm, at least one floating mass mounted to the diaphragm (at at least one coupling point of the diaphragm), and an acoustic transducer mounted to the floating mass. Preferably, each floating mass is configured and mounted so that as each floating mass and each coupling point of the diaphragm move in sympathy with acoustic waves (to be detected) that impinge on the diaphragm, the acoustic transducer rides with and is stabilized by the floating mass to which it is mounted and the diaphragm is stabilized by each floating mass. The acoustic transducer can be of any of many different types. For example, it can be a microphone, or an optical, capacitive, or inductive transducer. The diaphragm can have an isolating portion which absorbs acoustic surface wave energy incident thereon, or otherwise prevents or reduces transmission of acoustic surface waves through the isolating portion between regions of the diaphragm.

64 Claims, 22 Drawing Sheets

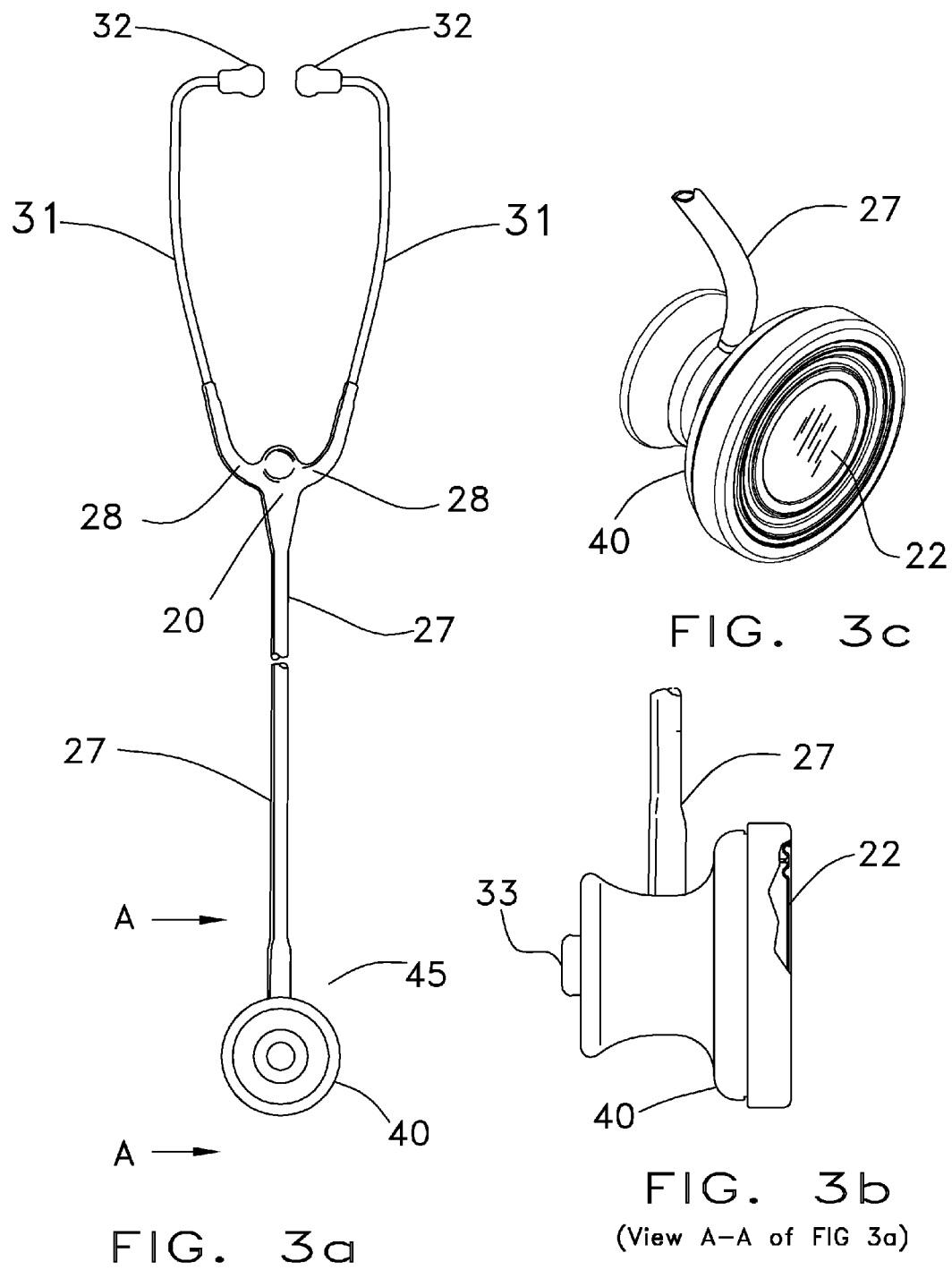

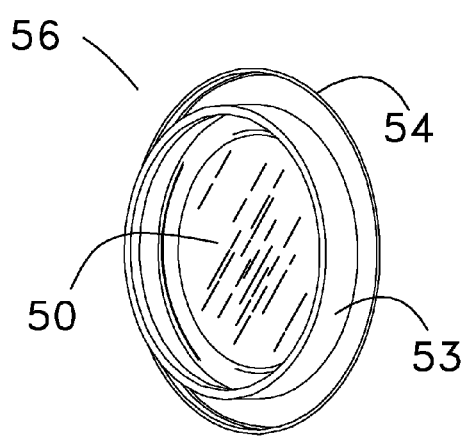
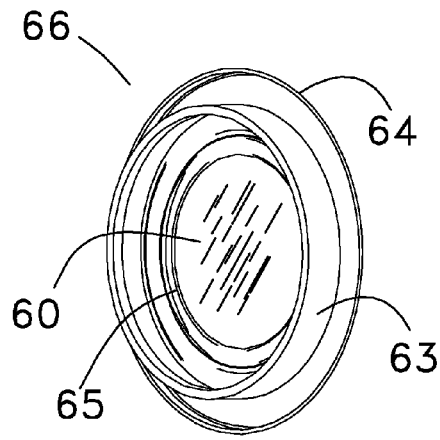
FIG. 4a
FIG. 5a
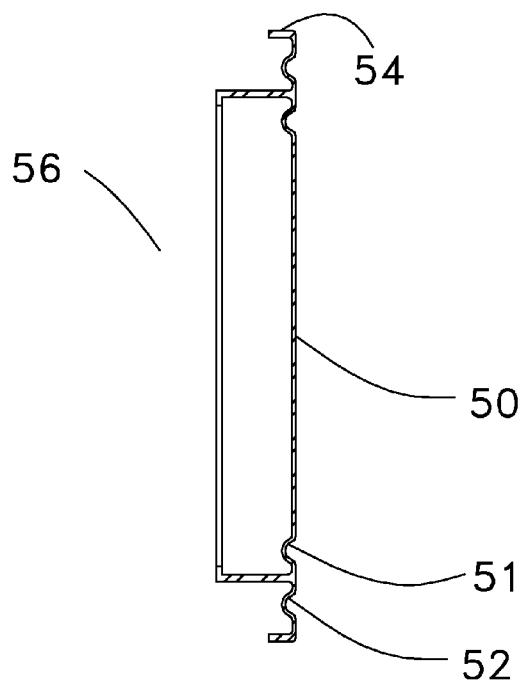
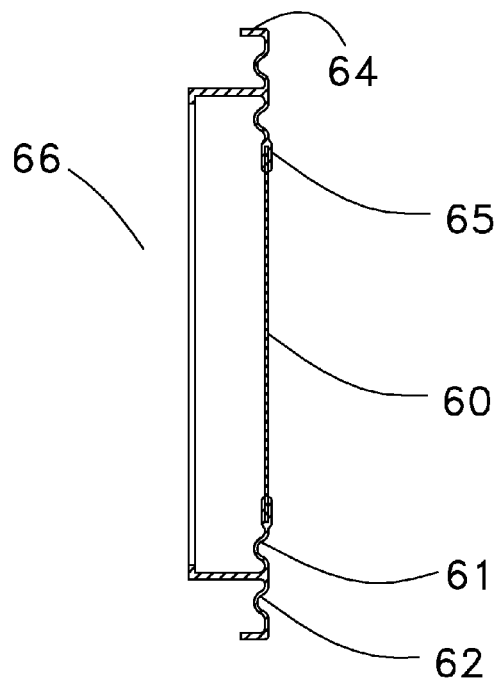
FIG. 4
FIG. 5

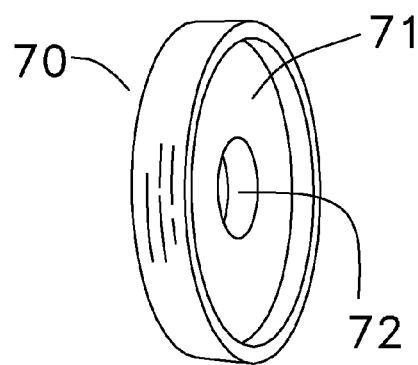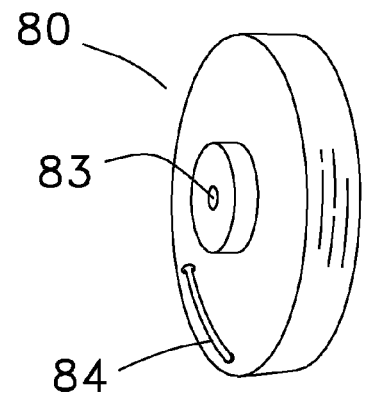
FIG. 6a          FIG. 7a
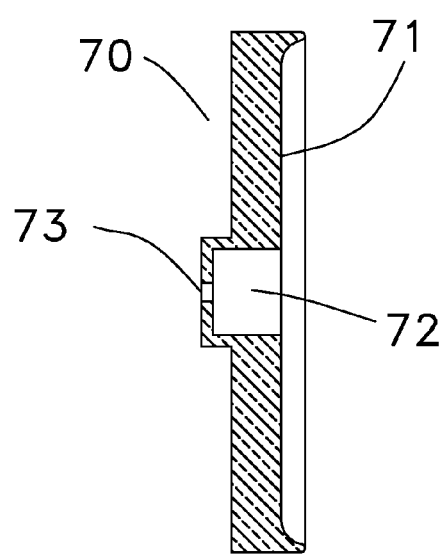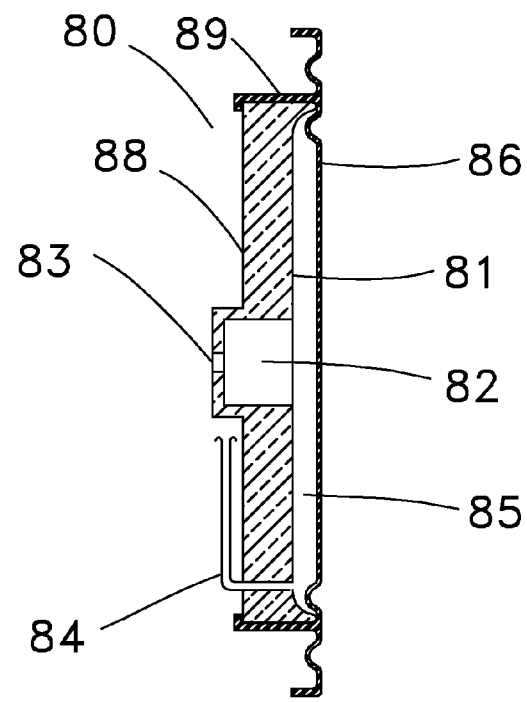
FIG. 6           FIG. 7

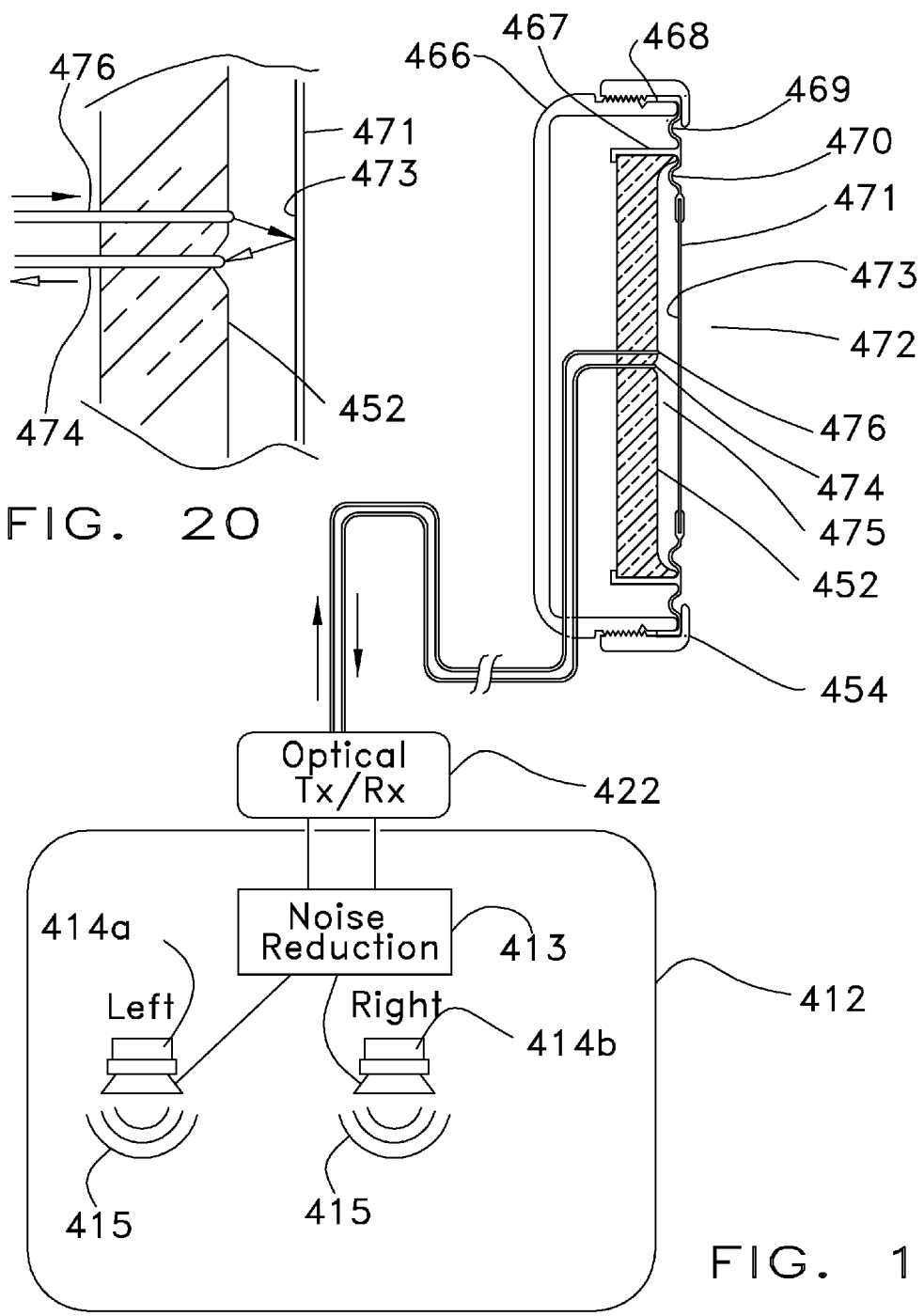

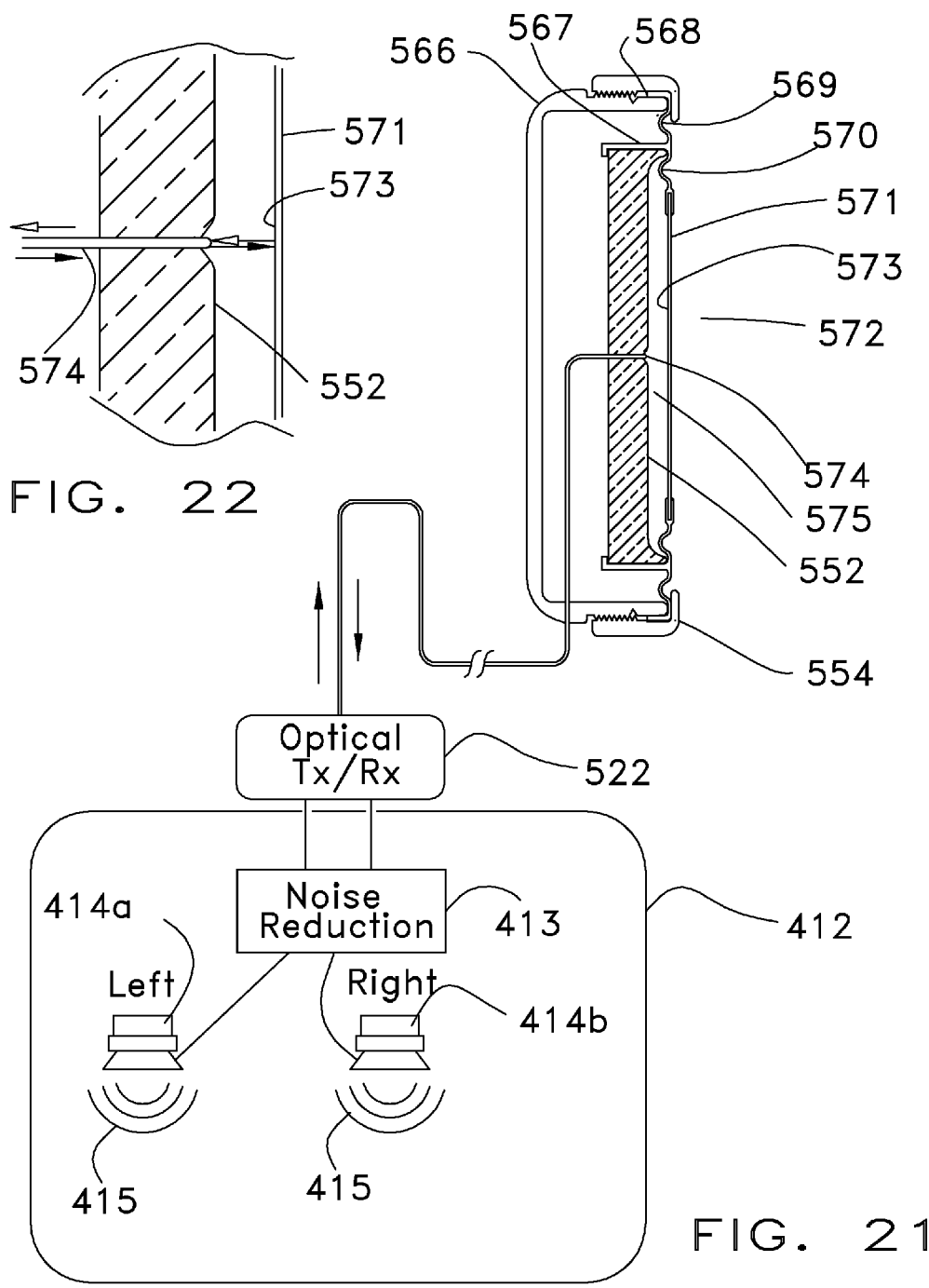

US 8,396,228 B2

FLOATING BALLAST MASS ACTIVE STETHOSCOPE OR SOUND PICKUP DEVICE

BACKGROUND

1. Field of the Invention

The present invention relates to detection of sounds and augmentation of detected sounds above ambient noise. In a class of embodiments, it relates to detection of sounds propagating from within human or animal bodies (e.g., sounds from the heart or lungs) using an active stethoscope configured to augment the sounds of interest above ambient noise.

2. Prior Art

Throughout this disclosure, including in the claims, the expression "active" stethoscope (or "active" sound detection device) denotes a stethoscope (or sound detection device) that includes an acoustic transducer useful for converting acoustic waves (e.g., body sounds of interest) into another form of energy.

Herein, the expression "electronic" stethoscope (or "electronic" sound detection device) denotes a stethoscope (or sound detection device) that includes an acoustic transducer useful for converting acoustic waves of interest (e.g., body sounds) into at least one electric signal. Also herein, the expression "passive" stethoscope (or "passive" sound detection device) denotes a stethoscope (or sound detection device) that does not include an acoustic transducer.

Throughout this disclosure, including in the claims, each of the expressions "acoustic transducer" and "sound transducer" denotes a device for converting acoustic waves into another form of energy. For example, one type of acoustic transducer is a typical microphone configured to convert acoustic waves into an electrical signal. Another example of an acoustic transducer is a device configured to convert acoustic waves into electromagnetic waves (e.g., visible radiation or electromagnetic radiation whose wavelength or wavelengths is or are outside the visible range), and optionally also to convert the electromagnetic waves into an electrical signal.

Acoustic transducers are sometimes referred to herein as sound pick-ups, and are sometime referred to herein simply as transducers.

Throughout this disclosure including in the claims, the expression that a first element is "mounted to" a second element denotes that the first element is attached or coupled in any manner to the second element at at least one point or region of the second element (each such point or region is denoted herein as a "coupling point"), such that when the second element moves (e.g., vibrates), the first element moves in phase with and in sympathy with the second element at each coupling point. A first element can be "mounted to" a second element if the two elements are directly attached to each other or if they are otherwise coupled to each other (e.g., coupled by any rigid coupling means) without freedom to move relative to each other at each coupling point. A first element can be "mounted to" a diaphragm (a flexible element) at at least one coupling point even if portions of the diaphragm other than each coupling point have freedom to move out of phase with the first element.

The expressions "mounted on" and "referenced to" are used herein as synonyms to the expression "mounted to," with reference to a floating mass that is mounted to a diaphragm.

Active and passive stethoscopes are used by health care givers (to be referred to herein as physicians since they are typically physicians) to aid in the detection of body sounds for the purpose of diagnosing various symptoms, for example, heart beat anomalies or lung infections. This procedure is commonly called auscultation. Stethoscope design is a specialty art, difficult to learn due to the low sound levels emitted by the body. Electronic stethoscopes have been used in the medical field for some time, with mixed success because body sound emissions are typically only a couple of Decibels (dB) above the background noise. Background noise is more precisely known as noise floor and will be referred as such in this disclosure.

The conventional stethoscope in its most primitive form consists of a closed space (often referred to as a "chest piece"), generally shaped like a round pill box, with one side consisting of a semi-flexible diaphragm and another side having a flexible tube attached. The flexible tube is generally molded at the far end into a "Y" shape which is applied to the physician's ears. In use, the diaphragm side of the chest piece is placed against the body surface so that sounds from the body cause the diaphragm to move in sympathy. The air space in the interior of the chest piece experiences minute pressure waves from the moving diaphragm. These pressure waves travel up the flexible tube and are perceived as sound by the physician's ears.

Such a conventional, passive stethoscope has several drawbacks, including the following: the perceived sound is very, very low in amplitude; the sound is colored by the absorptive characteristic of the flexible tube; and the sound is colored by the resonant characteristics of the air column in the flexible tube. Attempts have been made to improve these drawbacks such as careful material selection and finish of said flexible tube.

An additional and major improvement was to size the flexible tube of a passive stethoscope so its air column resonated at about 50 to 100 Hertz. (One company among many that specializes in this area is 3M Corporation with a line of stethoscopes generally called the Littmann line). The resonant air column augmented the detection of the heart beat greatly. However, the entire stethoscope's frequency response was colored towards the 50 to 100 Hertz frequency and its multiples. A recent example of a passive stethoscope having a resonant cavity for emphasizing detected sound frequencies within at least one predetermined frequency range is described in U.S. Pat. No. 4,270,627, issued to Raymond R. Hill. The diaphragm of the stethoscope described in the Hill patent (and other conventional stethoscopes) can include a thin, distally protruding probe attached to its center. In use, the probe moves in sympathy with the body sounds being detected, and thus the probe cannot have a high mass.

Much if not all of the medical community has been trained (e.g., many if not all cardiologists have been trained) using stethoscopes designed to emphasize detected sound frequencies within a predetermined frequency range (typically from about 50 to 100 Hertz) and in fact, a pure and perfect response stethoscope would sound strange to them. This pitfall was experienced by the earliest electronic stethoscopes.

An example of an electronic stethoscope designed with a goal of achieving purity in auscultation, without emphasizing detected sounds in a predetermined frequency range, is described in U.S. Pat. No. 6,498,854, issued Dec. 24, 2002, to Clive Smith. This patent teaches in detail the purity aspects of a totally unloaded stethoscope diaphragm. The diaphragm functions as an electrode of a capacitor, and its movement in response to body sounds is converted to an electric signal.

In practice it has been found favorable to design an electronic stethoscope which mimics the response of Littmann brand passive stethoscopes. An electronic stethoscope that mimics a resonant tube passive stethoscope is described in U.S. Pat. No. 6,587,564, issued Jul. 1, 2003, to Ronald Cusson. This patent describes a resonant chamber sound pick-up for an electronic stethoscope, including metal ballast, a sound pick-up rigidly attached to the ballast, a support cup, and closed cell, compliant foam between the ballast and support cup. A diaphragm (whose distal surface is designed to be placed against the patient's skin during use) is mounted to the compliant foam so as to define a resonant cavity between the sound pick-up and the diaphragm's proximal surface.

FIG. 1 is a stylized cross-sectional view of a first prior art electronic stethoscope chest piece which comprises a sound transducer 1 (which is typically a miniature microphone) mounted in a rigid body 3 held in a chest piece housing 4. Diaphragm 2 is mounted in front of (distally with respect to) transducer 1. Diaphragm 2 is held to housing 4 by a generally circular ring 9. Rigid body 3 is fastened to housing 4 by bosses 8 or some other rigid means.

The electronic stethoscope chest piece of FIG. 1 also includes electronic amplifier 5 and power source 6 for amplifier 5 (the power source is usually a battery). Amplified signals from microphone (or other transducer) 1 are sent along wires from amplifier 5 through stethoscope tube 7 to sound transducers (not shown), which are generally headphones, located at a stethoscope head piece (not shown) at the proximal end of stethoscope tube 7.

The entire construction of the FIG. 1 chest piece is relatively rigid. Diaphragm 2 is generally rigidly fastened to housing 4. Microphone (or other transducer) 1 has a largely isotropic characteristic. It picks up sound vibrations from all directions which include the diaphragm 2, rigid body 3, and housing 4. This first prior art electronic stethoscope chest piece has the poorest signal to noise performance of those described herein.

FIG. 2 is a stylized cross-sectional view of a second prior art electronic stethoscope chest piece, of the type described in above-cited U.S. Pat. No. 6,587,564 to Cusson. The chest piece of FIG. 2 comprises sound transducer 11 (typically a miniature microphone) mounted in a rigid body 13 held in a closed cell, compliant foam cup 18. This assembly is held in housing 14. In front of microphone 11 is placed a diaphragm 12 which is directly attached to foam cup 18, but not to rigid body 13. In this second prior art example, diaphragm 12 is not rigidly fastened to housing 14. The chest piece of FIG. 2 also includes electronic amplifier 15 and power source 16 for amplifier 15 (the power source is typically a battery). Amplified signals from microphone (or other transducer) 11 are sent along wires from amplifier 15 through stethoscope tube 17 to sound transducers (not shown), which are generally headphones, located at a stethoscope head piece (not shown) at the proximal end of stethoscope tube 17.

The prior art chest piece of FIG. 2 has significantly better signal to noise performance than the chest piece of FIG. 1 for two reasons: first, rigid body 13 of FIG. 2 is not rigidly fastened to housing 14 (whereas rigid body 3 of FIG. 1 is rigidly attached to housing 4); and second, diaphragm 12 of FIG. 2 is not rigidly fastened to housing 14 (whereas diaphragm 2 of FIG. 1 is rigidly attached to housing 4). The prior art chest piece of FIG. 2 also utilizes a resonant sound chamber 19 (and has a narrow vent that extends horizontally from the proximal wall of chamber 19) to augment frequencies in the 50 to 150 Hz range. An electronic stethoscope including the chest piece of FIG. 2 typically performs significantly better than one including the prior art chest piece of FIG. 1.

Most electronic stethoscopes exhibit poor signal-to-noise performance. The sound of the human heart and other body sounds at the skin level are only a dB or two above the threshold of human hearing. Also, general ambient noise is present at this low level. This presents a difficult, two-fold problem that affects all stethoscopes: (a) how to hear the low level (and typically very faint) heart sound or other body sound of interest; and (b) how to discriminate the body sound of interest from ambient noise. Other conventional sound detection devices for detecting low level sounds in the presence of noise are subject to this two-fold problem. The present invention addresses the problem in several ways.

SUMMARY OF THE PRESENT INVENTION

In a class of embodiments, the invention is an active sound detection device including a diaphragm, at least one floating mass mounted to the diaphragm (at at least one coupling point of the diaphragm), and an acoustic transducer (e.g., a microphone) mounted to the floating mass. The diaphragm is configured to be placed in contact with a surface (e.g., the skin of a patient) to which (or along which) acoustic waves to be detected propagate during operation of the device. In some embodiments, the device includes at least a first floating mass mounted to the diaphragm and a second floating mass mounted to the diaphragm, and the acoustic transducer is mounted to the first floating mass. Preferably, each floating mass is configured (e.g., has an appropriate weight) and is mounted such that as each floating mass and each coupling point of the diaphragm move in sympathy with acoustic waves to be detected (e.g., body sounds) as the acoustic waves impinge on the diaphragm, the acoustic transducer rides with and is stabilized by the floating mass to which it is mounted, and the diaphragm is stabilized by each said floating mass.

In some embodiments, the diaphragm of the inventive device includes multiple elements (e.g., the diaphragm is an assembly including multiple elements). For example, the diaphragm may include a central diaphragm membrane, one or more annular convolutions around the membrane, and a rim portion for attachment to a housing (e.g., a chest piece housing) of the device. In some embodiments, the device includes a housing to which an outer edge of the diaphragm is mounted, and the diaphragm has an isolating portion (which may include or consist of one or more annular convolutions of the diaphragm) between the outer edge and each coupling point of the diaphragm at which a floating mass is coupled to the diaphragm, and the floating mass is not mounted to (and has freedom to move relative to) the housing. Each isolating portion of the diaphragm is configured to absorb acoustic surface wave energy incident thereon (or otherwise to prevent or reduce transmission of acoustic surface waves through the isolating portion from one region of the diaphragm to another region of the diaphragm). In such embodiments including an isolating portion of the diaphragm, the floating mass moves in sympathy with each coupling point (at which it is mounted to the diaphragm) as the coupling point vibrates in response to body sound (or other sound to be detected), and the isolating portion of the diaphragm acoustically isolates the floating mass and each said coupling point from acoustic surface waves (that propagate along the diaphragm's inner and/or outer surface) and/or from acoustic waves that propagate from the housing (e.g., due to vibration of the housing). In another exemplary embodiment, an annular region of a floating mass (e.g., at the outer edge of the floating mass) is mounted to an annular region of the diaphragm between two annular convolutions of the diaphragm (e.g., an outer convolution near an outer edge of the diaphragm and an inner convolution between the annular region of the floating mass and the diaphragm's center) and the diaphragm's outer edge is attached to a housing;

Each floating mass, sometimes referred to herein as a "floating ballast mass" or simply as a "mass," is rigid in the following sense. During operation of the sound detection device, the floating mass moves in sympathy with and in phase with each coupling point of the diaphragm without significant deformation of the floating mass (i.e., the floating mass moves in sympathy without deforming, or deforms by no more than a minor amount while so moving).

A wide variety of different types of acoustic transducer can be included in different embodiments of the inventive device. In some embodiments, the acoustic transducer is a microphone which produces an electrical signal in response to acoustic input. In other embodiments, the acoustic transducer is an optical, capacitive, or inductive sound transducer.

It should be appreciated that the expression that a diaphragm includes a membrane portion (or a central membrane or a membrane) is used herein in a broad sense to cover cases in which the membrane or membrane portion is an integral portion of the entire diaphragm (or an element of the entire diaphragm), and also cases in which the membrane or membrane portion is not an integral portion of the entire diaphragm and is instead bonded (or otherwise attached) to at least one other separate piece or element of the diaphragm. Similarly, the expression that a diaphragm includes a rim (or isolating) portion is used herein in a broad sense to cover cases in which the rim (or isolating) portion is an integral portion of the entire diaphragm (or an element of the entire diaphragm), and also cases in which the rim (or isolating) portion is bonded (or otherwise attached) to at least one other separate piece or element of the diaphragm.

In typical embodiments, the inventive active sound detection device is an active stethoscope. In other embodiments, the inventive active sound detection device is not a stethoscope and is useful in non-stethoscope applications. An example of one such non-stethoscope application is detecting sounds in an object (other than a human or animal body) with the inventive device resting on a surface of the object, and with the inventive device providing acoustic isolation from noise from sources other than within the object (e.g., vibrations resulting from contact of the user's fingers with the device, and/or acoustic surface waves that propagate along the object's surface but have not originated from within the object). Herein, the term "stethoscope" denotes any instrument for listening to sound (body sound) propagating from within a human or animal body.

In a class of embodiments, the inventive active sound detection device is an active stethoscope including a chest piece (including a diaphragm, at least one floating mass mounted to the diaphragm, and an acoustic transducer mounted to one said floating mass), and a headset coupled (e.g., by a tube) to the chest piece. The headset includes at least one output transducer (e.g., a pair of earphones). In some embodiments in this class, the acoustic transducer generates at least one electrical signal in response to body sounds that cause the diaphragm to move, and each output transducer is coupled and configured to convert at least one said electrical signal into sound that is audible to a physician or other user. In other embodiments in this class, the acoustic transducer produces a transducer output in response to body sounds that cause movement of the diaphragm, and the stethoscope includes headset driving circuitry coupled to the acoustic transducer and each output transducer. The headset driving circuitry is configured to generate at least one electrical signal in response to the transducer output (which may, for example, be an optical signal), and each output transducer is coupled and configured to convert at least one said electrical signal into sound that is audible to a user.

A stethoscope designed in accordance with typical embodiments of the invention includes a chest piece having a body which supports the diaphragm, and each floating mass is mounted to the diaphragm but not to the body. Typically, each floating mass is separated from the body by an isolating portion of the diaphragm, and has freedom to move relative to the body. The isolating portion (which may include or consist of one or more annular convolutions of the diaphragm) is configured to absorb acoustic surface wave energy incident thereon, or otherwise to prevent or reduce transmission of acoustic surface waves through the isolating portion from one region of the diaphragm to another region of the diaphragm. Preferably, each floating mass is acoustically isolated from the body but acoustically coupled to the diaphragm (because it is mounted thereto), and has freedom to move in phase with and in sympathy with each diaphragm coupling point (at which the floating mass is coupled to the diaphragm).

In preferred embodiments, the present invention addresses the above-noted, two-fold problem of conventional stethoscopes and other sound detection devices in one or more (e.g., all) of the following five ways:

the acoustic transducer of the inventive sound detection device is mounted to the floating mass and the floating mass is mounted to the diaphragm, such that the floating mass stabilizes the acoustic transducer during operation of the device;

preferred embodiments of the inventive sound detection device (including active stethoscope embodiments) that provide a closed chamber resonance to augment sounds (e.g., heart sounds and/or other body sounds) to be detected;

in some preferred embodiments, the floating mass is acoustically isolated from noise due to vibrations (e.g., vibrations resulting from physician finger movement) of a housing (e.g. a stethoscope chest piece housing) that supports the diaphragm, and/or from acoustic surface waves (e.g., surface waves that propagate to the diaphragm's periphery and from the periphery toward the diaphragm's center). For example, in some such embodiments the diaphragm (e.g., an outer edge of the diaphragm) is mounted to the housing, and the floating mass is separated from the housing by an isolating portion of the diaphragm (e.g., a convoluted region of the diaphragm) which surrounds each coupling point of the diaphragm and prevents (or reduces) transmission of acoustic surface waves through the isolating portion to the floating mass, so that the floating mass is not mounted to the housing and is acoustically isolated at least to a degree from the housing. With such a configuration, the floating mass moves in sympathy with each coupling point of the diaphragm when the diaphragm vibrates in response to body sound (or other sound to be detected), and the isolating portion acoustically isolates the floating mass and each coupling point from acoustic surface waves and from vibration of the housing. In another exemplary embodiment, an annular region of the floating mass (e.g., a rim portion of the floating mass) is mounted to an annular coupling region of the diaphragm between two isolating portions of the diaphragm (e.g., an outer annular convolution near the diaphragm's rim and an inner annular convolution between the annular region of the floating mass and the diaphragm's center) and a rim portion of the diaphragm is attached to the housing. The isolating portions prevent or reduce transmission of acoustic surface waves through said isolating portions to the diaphragm's annular coupling region and the floating mass;

preferred embodiments of the inventive stethoscope or other sound detection device include acoustic damping materials (preferably advanced noise damping materials) that cover at least some of the device's body and/or internal parts; and preferred embodiments of the inventive stethoscope or other sound detection device include a complex diaphragm that includes damping material (preferably advanced sound deadening material) that prevents ambient noise from reaching an interface between the patient's skin and a sensitive portion of the diaphragm.

In some embodiments, the inventive sound detection device includes two or more transducers: an acoustic transducer referenced (mounted) to the floating mass which converts acoustic waves of interest into another form (e.g., into optical or other electromagnetic waves, or into an electrical signal), and a second transducer (which may be located in a chest piece also containing the acoustic transducer, or in a headset or another location remote from a chest piece containing the acoustic transducer). The second transducer is coupled and configured to convert the acoustic transducer's output into another form (e.g., to convert optical radiation from the acoustic transducer into an electrical signal). Optionally, the device also includes at least one additional transducer (e.g., headset transducers which convert an electrical signal from the second transducer into sound that is audible to a physician or other user).

The design of preferred embodiments of the inventive active stethoscope departs from conventional resonant air column designs while providing a resonant chamber in the stethoscope's chest piece behind the diaphragm as do conventional resonant air column designs. These preferred embodiments represent an advance over the design described in cited U.S. Pat. No. 6,587,564 to Cusson in that they incorporate a floating mass mounted to the stethoscope diaphragm (at one or more coupling points of the diaphragm) and an acoustic transducer referenced to the floating mass. The floating mass has freedom to move in sympathy with the diaphragm's coupling point (or points), relative to the body of the stethoscope's chest piece, so as to stabilize the diaphragm. The stethoscope's acoustic transducer (e.g., microphone) rides with the floating mass to which it is mounted as the floating mass moves during detection of body sound. The floating mass thus stabilizes the acoustic transducer as well as the diaphragm. In typical use, the patient's skin also provides damping to reduce noise that would otherwise reach the acoustic transducer. In preferred embodiments, the floating mass contributes a capacitive acoustic impedance, and the diaphragm contributes a resistive acoustic impedance, to the acoustic impedance of the structure that supports the acoustic transducer.

Preferred embodiments of the inventive stethoscope include a diaphragm having a novel design with a plurality of concentric convolutions on its face. In some such embodiments, an annular region of the diaphragm is attached to the floating mass, and the diaphragm has a first annular convolution radially inside this annular region and a second annular convolution radially outside this annular region to help to isolate the floating mass acoustically from noise sources. Other embodiments of the invention employ a diaphragm that does not have concentric convolutions on its face. By implementing embodiments of the present invention with appropriate materials, the same or better signal to noise performance may be achievable with diaphragms that do not have concentric convolutions on their faces and with diaphragms that do have concentric convolutions on their faces.

Electronic noise cancelling techniques are optional when implementing the present invention but are implemented in some embodiments. It is well known how to implement electronic (or active) noise cancellation in stethoscopes, and many commercially available electronic stethoscopes implement such noise cancellation. The inventor's study of a variety of commercial electronic stethoscopes that implement active noise cancellation revealed a "sameness" of body sounds detected from patient to patient using all such stethoscopes. This is analogous to all Model T Fords coming in any color from the factory . . . as long as it's black. It is believed that the primary reason for this sameness is that conventional electronic noise cancellation is imperfect and tends to artificially shape the audio signal to a pre-determined bell curve response that engineers have designed. Subtle timbre of the sounds emanating from the patient's body can be a key diagnostic artifact for the trained physician. It is expected that embodiments of the inventive stethoscope that lack means for electronic noise cancellation can be implemented so as to produce a sound output that allows these sound nuances to be heard. Despite this, it is expected that noise cancelling technologies useful in stethoscopes will probably improve in the future and will not be as primitive as they are at present.

BRIEF DESCRIPTION OF THE DRAWINGS

FIG. 3a is an elevational view of a first embodiment of the inventive stethoscope.

FIG. 3b is a side elevational view of the chest piece of the FIG. 3a embodiment of the inventive stethoscope, viewed from between points A-A of FIG. 3a.

FIG. 3c is a perspective view of the chest piece of FIG. 3b.

FIG. 3d is a side cross-sectional view of the chest piece of FIGS. 3b and 3a.

FIG. 4 is a side cross-sectional view of a convoluted diaphragm of one embodiment of the present invention.

FIG. 4a is a perspective view of the convoluted diaphragm of FIG. 4.

FIG. 5 is a side cross-sectional view of a convoluted diaphragm of a second embodiment of the present invention.

FIG. 5a is a perspective view of the convoluted diaphragm of FIG. 5.

FIG. 6 is a side cross-sectional view of a mass cup (floating mass) of one embodiment of the present invention.

FIG. 6a is a perspective view of the mass cup of FIG. 6.

FIG. 7 is a side cross-sectional view of a mass cup (floating mass) and a diaphragm coupled thereto, in accordance with a second embodiment of the present invention.

FIG. 7a is a perspective view of the mass cup of FIG. 7.

FIG. 19 is a side cross-sectional view of an embodiment of the inventive stethoscope including a non-powered optical chest piece (which includes an optical sound transducer that converts body sounds into optical or other electromagnetic radiation) and a headset (412) including noise canceling output sound transducers. The stethoscope also includes optical transmitter and receiver circuitry which is typically located remotely from the chest piece (e.g., in a different room than the chest piece) during use, and is configured to receive and convert the output of the chest piece into an electrical signal for assertion to noise reduction circuitry in the headset.

FIG. 20 is an enlarged detail of the non-powered optical chest piece of FIG. 19.

FIG. 21 is a side cross-sectional view of another embodiment of the inventive stethoscope including a non-powered optical chest piece (including an optical sound transducer that converts body sounds into optical or other electromagnetic radiation) and a headset (412) including noise canceling output sound transducers. The stethoscope also includes optical transmitter and receiver circuitry which is typically located remotely from the chest piece (e.g., in a different room than the chest piece) during use, and is configured to receive and convert the output of the chest piece into an electrical signal for assertion to noise reduction circuitry in the headset.

FIG. 22 is an enlarged detail of the non-powered optical chest piece of FIG. 21.

DETAILED DESCRIPTION OF THE PREFERRED EMBODIMENTS

Many embodiments of the present invention are technologically possible. It will be apparent to those of ordinary skill in the art from the present disclosure how to implement them.

First Stethoscope Embodiment

Figure 1:
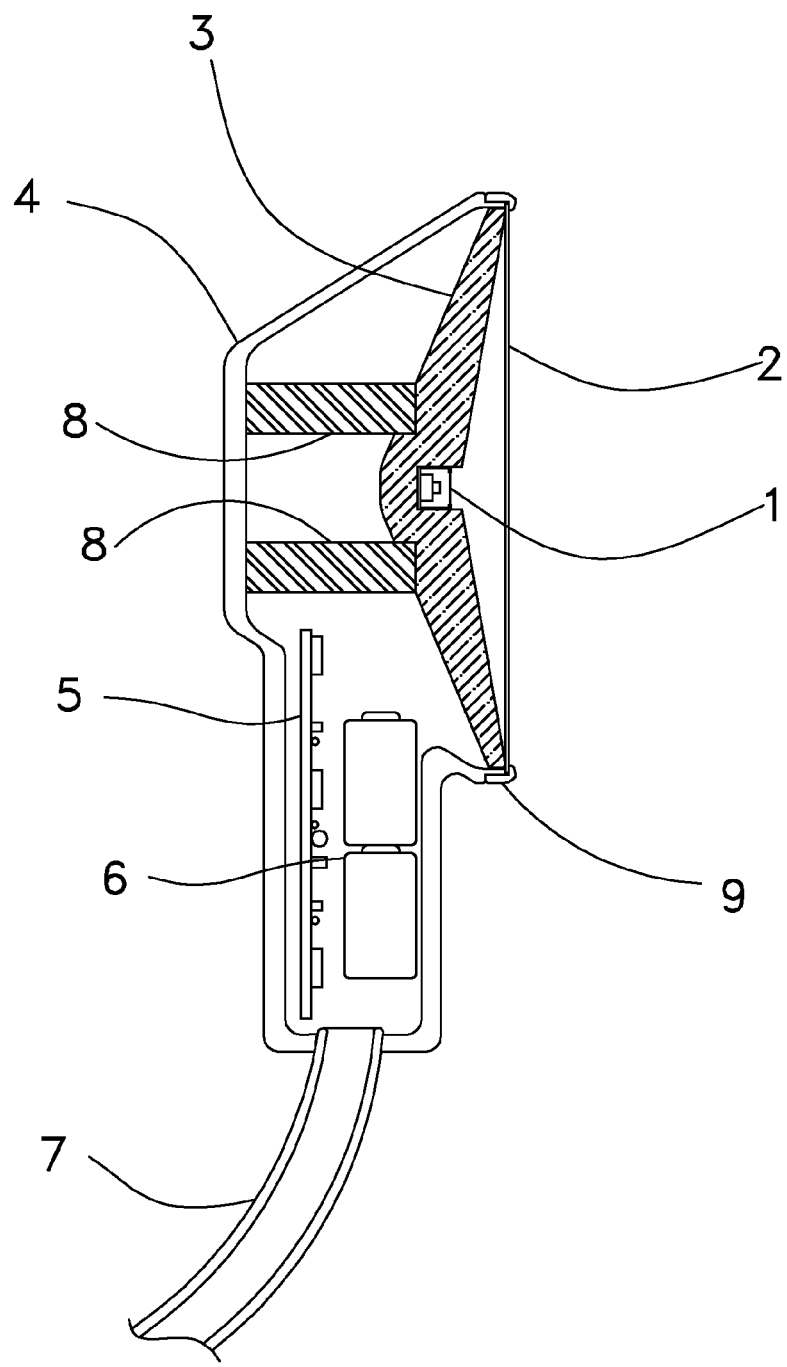
FIG. 1 is a side cross-sectional view of a portion of a first prior art electronic stethoscope showing the basic internal structure.
Figure 2:
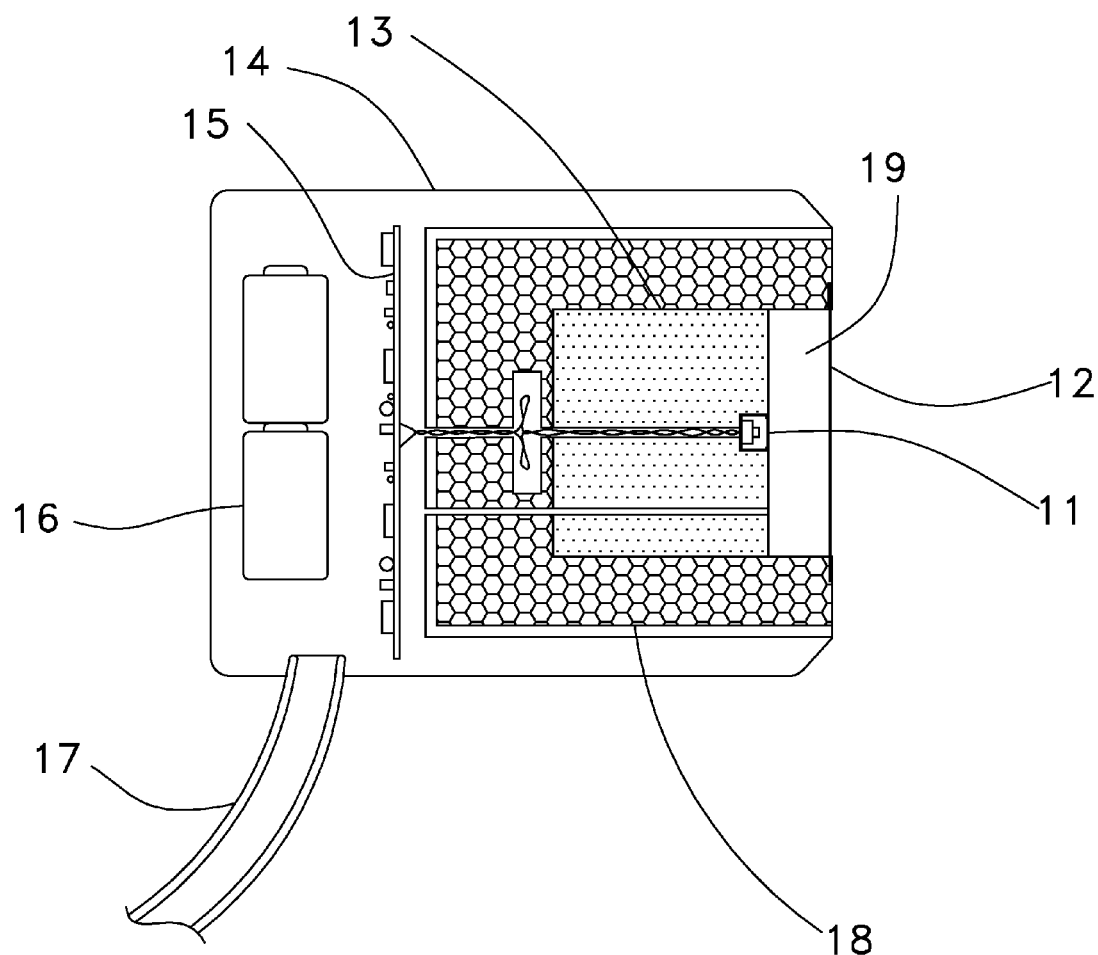
FIG. 2 is a side cross-sectional view of a portion of a second prior art electronic stethoscope showing the basic internal structure.
Figure 3D:
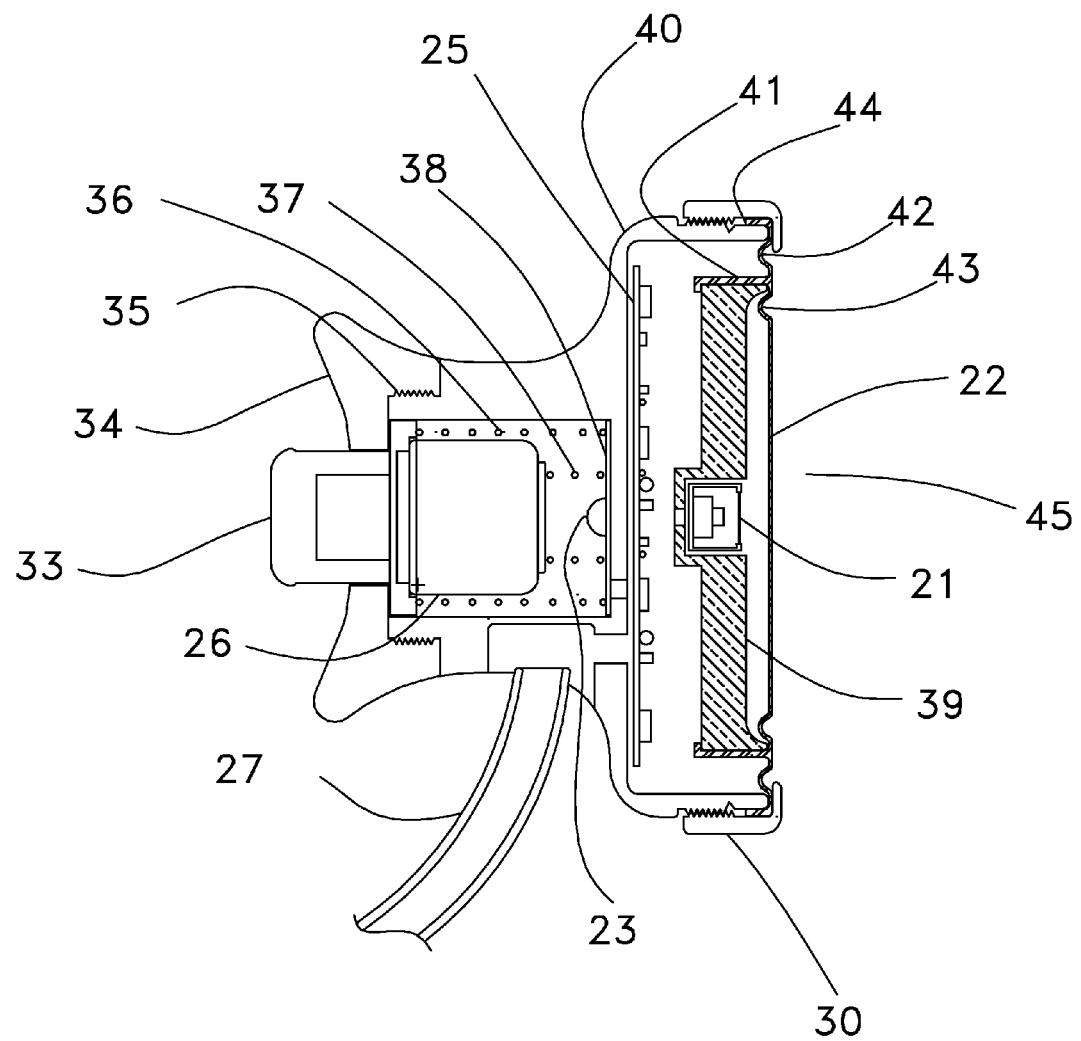

FIGS. 3*a*, 3*b*, 3*c* and 3*d* are views of a first embodiment of an electronic stethoscope chest piece designed according to the present invention. With reference to FIG. 3*a*, this stethoscope includes stethoscope chest piece 45 (having body or "housing" 40) and stethoscope tube 27 terminating in a "Y" section 20. Arms 28 of section 20 are provided with two ear piece tubes 31, each terminating at an ear tip 32. These ear tips 32 can be fitted with earphone sound transducers (a common practice in the electronic stethoscope art) or sound output transducers can be placed elsewhere. Examples of various output transducers that can be employed in variations on the FIG. 3*a* embodiment (and other embodiments of the invention) to provide audible sound output to the physician (or other user) are disclosed herein.

FIG. 3*b* is a side elevational view of the chest piece of the FIG. 3*a* embodiment of the inventive stethoscope, viewed from between points A-A of FIG. 3*a*, with a small cutout to expose a diaphragm 22. FIG. 3*c* is an overall perspective view of the stethoscope chest piece.

Referring to FIG. 3*d*, stethoscope chest piece 45 includes chest piece housing 40, floating mass 39, and sound transducer 21 (which is preferably a miniature microphone as shown in the figure) mounted to floating mass 39. Mass 39 is held in housing 40 by an extension cup 41 that extends from a specially molded diaphragm 22. Diaphragm 22 is clamped by clamp ring 30 to housing 40, by screwing a threaded portion of ring 30 onto a complementary threaded end portion of housing 40 (with rim portion 44 of the diaphragm between elements 30 and 40). Mass 39 is held in cup 41 (which is a cup-like molding extension of diaphragm 22) by pressure of fit. Mass 39 can alternatively be glued or mounted to diaphragm 22 by any other means known in the art.

Diaphragm 22 has a central portion which is a thin membrane, a rim portion 44, flexible annular convolutions 42 and 43 between the central and rim portions, and an extension cup 41. As shown in FIG. 3*d*, extension cup 41 is molded so as to protrude from the approximate midpoint of annular convolutions 42 and 43, and functions as a coupling point at which mass 39 is mounted to diaphragm 22. This position of cup 41 provides the central membrane portion of diaphragm 22 some freedom to move with respect to mass 39 while mass 39 (held in the extension cup 41) can move freely with respect to housing 40.

When diaphragm 22's distal face (the right face in FIG. 3*d*) is placed against a patient's skin, both diaphragm 22 and mass 39 (with microphone 21) freely float on the skin (mass 39 is free to move in sympathy with diaphragm 22) while body 40 and clamp ring 30 are acoustically isolated somewhat from diaphragm 22 and mass 39 (and thus from microphone 21) by the annular convolutions 42 and 43. This results in a natural improvement in the signal to noise performance of the stethoscope. Although two annular convolutions 42 and 43 are shown, variations on diaphragm 22 are implemented with more than or less than two such convolutions.

Each of annular convolutions 42 and 43 is an isolating portion of the diaphragm configured to absorb acoustic surface wave energy incident thereon from another region of the diaphragm (or otherwise to prevent or reduce transmission of acoustic surface waves therethrough from one region of the diaphragm to another region of the diaphragm). In variations on the described embodiment, diaphragm 22 lacks one or both of annular convolutions 42 and 43 but includes another isolating portion configured to prevent or reduce transmission of acoustic surface waves therethrough from at least one other region of the diaphragm to the floating mass, or diaphragm 22 lacks any isolating portion.

The volume between diaphragm 22, mass 39, and transducer 21 is a resonant chamber. In variations on the embodiment of FIGS. 3a-3d in which floating mass 39 is replaced by a vented floating mass (e.g., vented mass 80 of FIG. 7) that is vented to another space, or the device's resonant chamber (e.g., a chamber between the diaphragm and the distal face of the floating mass) is otherwise acoustically coupled to another chamber or space, such venting or acoustic coupling of the resonant chamber can alter the inventive device's resonant frequency response.

The electronic stethoscope of FIGS. 3a-3d also includes electronic amplifier 25 and power source 26 (which is usually, but not necessarily, a battery) coupled to amplifier 25. Amplified signals (indicative of microphone's 21 output) are sent along wires from amplifier 25 through stethoscope tube 27 to sound transducers, which are typically miniature headphones located in ear tips 32 of the stethoscope head piece connected to stethoscope tube 27. A momentary push button switch 33 is provided on the stethoscope chest piece's proximal face (the left face in each of FIGS. 3b and 3d). Switch 33 is actuated to overcome opposing force exerted thereon by springs 36 and 37, to push battery 26 against contact 23 thus turning the stethoscope on when auscultation is desired. The described switching technique is only for example. There are numerous switching methods available to those of ordinary skill in the art which can be used in alternative embodiments of the inventive device.

Battery cap 34 holds both switch button 33 and battery 26 in place by threads 35 machined into battery cap 34 and body 40. To those practiced in the art, switch and battery arrangements are manifold and any of numerous switching and powering methods available to those of ordinary skill in the art can be used in alternative embodiments of the inventive device.

Second Stethoscope Diaphragm Embodiment

FIGS. 4 and 4a show convoluted diaphragm 56 which is an embodiment of the inventive convoluted diaphragm that can replace diaphragm 22 in the device of FIGS. 3a-3d or be used in another embodiment of the inventive sound detection device. Diaphragm 56 has a central portion 50 which is a thin membrane, a rim portion 54, an inner annular convolution 51, an outer annular convolution 52, and an extension cup 53. Extension cup 53 is designed to hold mass 39 (of FIGS. 3a-3d) in the same way as does cup 41 in FIG. 3d. Extension cup 53 is molded so as to protrude from the approximate midpoint of annular convolutions 51 and 52, and functions as a coupling point at which mass 39 is mounted to diaphragm 56. Diaphragm 56 is typically made of a synthetic elastomer such as silicone or polyurethane. Those of ordinary skill in the art will recognize that many other materials may be used to form diaphragm 56, and such other materials are used in alternative embodiments of the inventive diaphragm. Although only two convolutions 51, 52 are shown, more or less than two are used in alternative embodiments of the inventive diaphragm.

Third Stethoscope Diaphragm Embodiment

FIG. 5 and FIG. 5a show convoluted diaphragm 66 which is another embodiment of the inventive convoluted diaphragm that can replace diaphragm 22 in the device of FIGS. 3a-3d or be used in another embodiment of the inventive sound detection device. Diaphragm 66 comprises two pieces (typically made of different materials): a thin relatively stiff membrane 60; and a second piece comprising rim portion 64, inner annular convolution 61, outer annular convolution 62, annular protrusion 65, and extension cup 63. Extension cup 63 is designed to hold mass 39 (of FIGS. 3a-3d) in the same way as does cup 41 in FIG. 3d. Extension cup 63 is molded so as to protrude from the approximate midpoint of annular convolutions 61 and 62, and functions as a coupling point at which mass 39 is mounted to diaphragm 66. Membrane 60 is typically insert-molded into annular protrusion 65 of the second piece of diaphragm assembly 66, so that annular protrusion 65 around membrane 60 holds the two pieces together. Alternatively, methods other than insert molding are used to assemble or otherwise form the diaphragm assembly 66 and variations thereon.

The materials used to manufacture diaphragm assembly 66 are typically a synthetic elastomer for the flexible parts 61-65 and fiberglass for the stiff membrane 60. Those of ordinary skill in the art will recognize that many other materials may be used to form diaphragm 66, and such other materials are used in alternative embodiments of the inventive diaphragm. Although only two convolutions 61 and 62 are shown, more than two or less than two (e.g., none) may be used in variations on the design shown in FIGS. 5 and 5a.

First Stethoscope Mass Cup Embodiment

FIG. 6 is a side cross-sectional view of mass cup 70 (a floating mass) which can replace mass 39 in the device of FIGS. 3a-3d or be used in another embodiment of the inventive sound detection device. FIG. 6a is a perspective view of mass cup 70 of FIG. 6. Mass cup 70 is generally disc shaped with a cupped face 71 and a recess 72 to hold a microphone or other sound transducer. There is also an opening 73 in the rear of the mass cup 70 to allow electrical connections to the microphone or other sound transducer.

Mass cup 70 can be made of a metallic material such as lead or bismuth tin alloy or a synthetic plastic composite material such as bismuth alloy impregnated polyurethane. Alternatively, mass cup 70 (and/or other embodiments of the inventive floating mass) can be a high density polymer, such as a high density polymer commercially sold as a proprietary compound by several companies (e.g., E.A.R. Corporation). In some embodiments, the mass cup can be formed from powdered or loose micro/macro spheres made of pure or alloy materials (e.g., lead or lead-tin shot). Those of ordinary skill in the art will recognize that many other materials may be used to form the inventive floating mass, and such other materials are used in alternative embodiments of the inventive floating mass.

Second Stethoscope Mass Cup Embodiment

FIGS. 7 and 7a are perspective and cross sectional views of mass cup 80, another floating mass which can replace mass 39 in the device of FIGS. 3a-3d or be used in another embodiment of the inventive sound detection device. Mass cup 80 is generally disc shaped with a cupped face 81 and a recess 82 to hold a microphone or other sound transducer. There is also an opening 83 in the rear of the mass cup 80 to allow electrical connections to the microphone or other sound transducer. Vent pipe 84 extends through mass cup 80 from the distal (front) face 81 to the proximal (rear) face 88 of mass cup 80. The purpose of vent pipe 84 is to vent the space (85) between face 81 and the diaphragm to which mass cup 80 is mounted during use (e.g., diaphragm 86 of FIG. 7). Varying the diameter or length of vent pipe 84 alters the resonant frequency response of an active stethoscope including diaphragm 86 (or another diaphragm) and mass cup 80 coupled to the diaphragm. Although not shown in FIG. 7, a suitable vent (performing the same function as does vent pipe 84) can alternatively be machined directly into the mass cup itself, for example, by drilling into the mass cup directly or machining a spiral vent on rear face 88 which can then be covered with a flat washer-like piece of material to match the original rear face 88. Another way to form such a vent is to machine a groove around a part of the circumference of mass cup 80, which when mounted to cup-like molding extension 89 of diaphragm 86 (or a similar molding extension of another diaphragm) would form a circumferential channel. In this case, drilling or machining would also have to be done to vent the channel both to the outside on one end, and into closed space 85 on the other end. Any of a variety of techniques known in the art can be employed to vent the closed space 85 in alternative embodiments of the invention. In general, it is preferable to provide a venting channel of appropriate length (to vent the space 85) as cost effectively as possible.

Mass cup 80 is typically made of a metallic material such as lead or a synthetic plastic composite material such as bismuth alloy impregnated polyurethane. Those of ordinary skill in the art will recognize that many other materials may be used to form mass cup 80 (and other embodiments of the inventive floating mass), and such other materials are used in alternative embodiments of the inventive floating mass.

Some embodiments of the inventive stethoscope are further improved by incorporating external and/or internal sound damping material to suppress housing body resonances and attenuate external sounds. For example, the housing of stethoscope chest piece 112 of FIG. 8 is sheathed with sound damping material 95, and stethoscope chest piece 142 of FIG. 9 has a sheath 123 made of a sound damping material inside chest piece housing 136.

Second Stethoscope Embodiment

Figure 8:
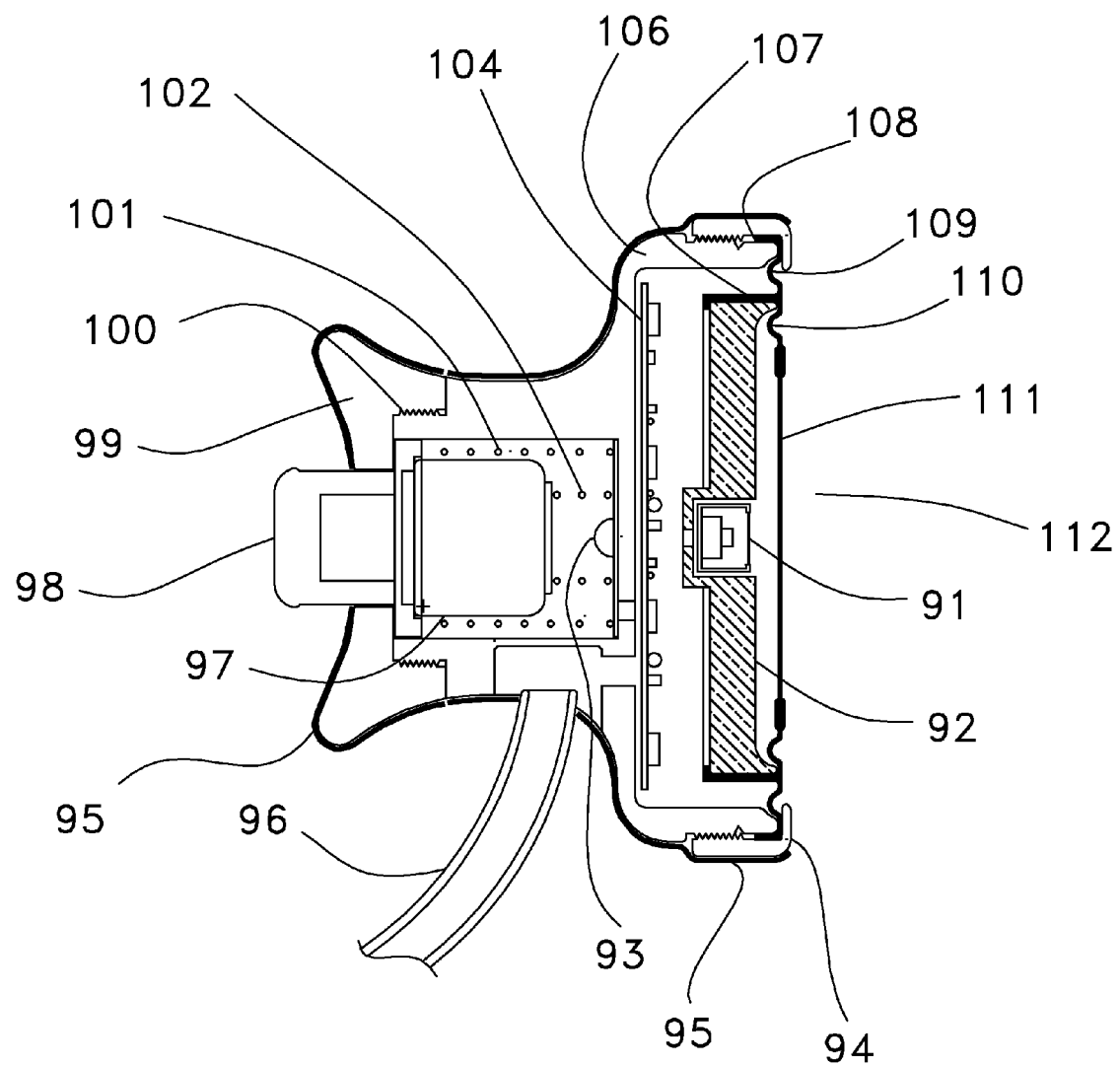
FIG. 8 is a side cross-sectional view of an embodiment of the present invention which includes a damped housing.

FIG. 8 is a stylized half section of a second embodiment of the inventive electronic stethoscope chest piece, which includes housing 106, floating mass 92, specially molded diaphragm assembly 108-111, and sound transducer 91 (which can be a miniature microphone) mounted to floating mass 92. Mass 92 is mounted to diaphragm assembly 108-111 in housing 106. More specifically, mass 92 is held (by pressure of fit) in cup-like molding extension 107 of assembly 108-111, which extends out from the rest of assembly 108-111 as shown. In variations on the FIG. 8 embodiment, mass 92 is mounted (e.g., glued or fastened) to assembly 108-111 by other suitable means.

Diaphragm assembly 108-111 includes thin, relatively stiff, central membrane portion 111, rim portion 108, annular convolutions 109 and 110, and extension cup 107 which protrudes in the proximal direction from between convolutions 109 and 110. As shown in FIG. 8, extension cup 107 is molded at the approximate midpoint of annular convolutions 109 and 110. The design of the FIG. 8 device allows diaphragm portion 111 to move (e.g., vibrate) with respect to mass 92, while mass 92 (held in extension cup 107), diaphragm portion 111, and each other portion of the diaphragm assembly in contact with the patient's skin move freely with respect to housing 106.

When chest piece 112's distal face (the right face in FIG. 8) is placed against a patient's skin, both diaphragm membrane 111 and mass 92 freely float on the skin while body 106 and clamp ring 94 (which holds diaphragm rim 108 against housing 106) are isolated somewhat from diaphragm membrane 111 and mass 92, and thus from microphone 91, by the annular convolutions 109 and 110. This results in a natural improvement in the signal to noise performance of the stethoscope. Although two annular convolutions 109 and 110 are shown, more, or less can be used if desired.

The electronic stethoscope of FIG. 8 also includes electronic amplifier 104 and a power source 97, which is usually but not necessarily a battery. Amplified signals from the microphone are sent along wires from amplifier 104 through stethoscope tube 96 to output sound transducers, which are generally headphones (not shown) located at the stethoscope head piece (not shown) connected to stethoscope tube 96.

Momentary push button switch 98 can be actuated to overcome opposing force exerted thereon by springs 101 and 102 so as to push battery 97 against contact 93, thus turning the stethoscope on when auscultation is desired. The described switching technique is only for example. There are numerous switching methods available to those of ordinary skill in the art which can be used in alternative embodiments of the inventive device.

Surrounding body 106 and clamp ring 94 is a thin sheath 95 made of a sound damping material (e.g., silicone rubber) designed to dampen resonances of the stethoscope body 106. Damping material 95 also acts as an external sound attenuator adding several dB to the sound detection device's signal to noise performance.

Third Stethoscope Embodiment

Figure 9:
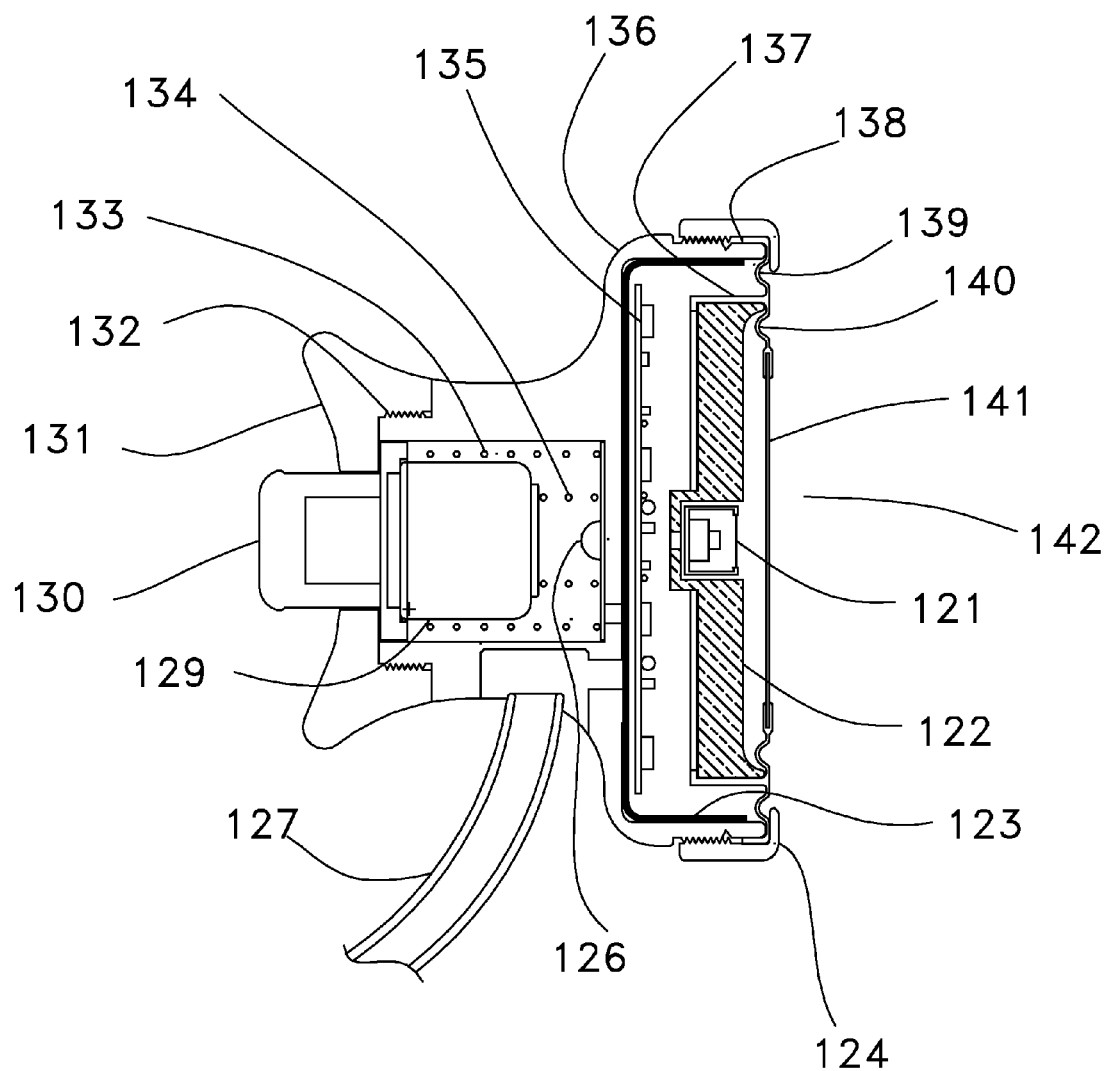
FIG. 9 is a side cross-sectional view of another embodiment of the present invention which includes a damped housing.

FIG. 9 is a stylized half section of a third embodiment of the inventive electronic stethoscope chest piece 142, which includes housing 136, floating mass 122, specially molded diaphragm assembly 137-141, and sound transducer 121 (which can be a miniature microphone) mounted to floating mass 122. Mass 122 is mounted to diaphragm assembly 137-141 in housing 136. More specifically, mass 122 is held (by pressure of fit) in cup-like molding extension 137 of assembly 137-141, which extends out from the rest of assembly 137-141 as shown. In variations on the FIG. 9 embodiment, mass 122 is mounted (e.g., glued or fastened) to assembly 137-141 by other suitable means.

Diaphragm assembly 137-141 includes thin, central membrane portion 141, rim portion 138, annular convolutions 139 and 140, and extension cup 137 which protrudes in the proximal direction from between convolutions 139 and 140. As shown in FIG. 9, extension cup 137 is molded at the approximate midpoint of annular convolutions 139 and 140. The design of the FIG. 9 device allows diaphragm portion 141 to move (e.g., vibrate) with respect to mass 122, while mass 122 (held in extension cup 137), diaphragm portion 141, and each other portion of the diaphragm assembly in contact with the patient's skin move freely with respect to housing 136.

When chest piece 142's distal face (the right face in FIG. 9) is placed against a patient's skin, both diaphragm membrane 141 and mass 122 freely float on the skin while body 136 and clamp ring 124 (which holds diaphragm rim 138 against housing 136) are isolated somewhat from diaphragm membrane 141 and mass 122, and thus from microphone 121, by the annular convolutions 139 and 140. This results in a natural improvement in the signal to noise performance of the stethoscope. Although two annular convolutions 139 and 140 are shown, more, or less can be used if desired.

The electronic stethoscope of FIG. 9 also includes electronic amplifier 135 and a power source 129, which is usually but not necessarily a battery. Amplified signals from the microphone are sent along wires from amplifier 135 through stethoscope tube 127 to output sound transducers, which are generally headphones (not shown) located at the stethoscope head piece (not shown) connected to stethoscope tube 127.

Momentary push button switch 130 can be actuated to overcome opposing force exerted thereon by springs 133 and 134 to push battery 127 against contact 126, thus turning the stethoscope on when auscultation is desired. The described switching technique is only for example. There are numerous switching methods available to those of ordinary skill in the art which can be used in alternative embodiments of the inventive device.

Inside housing 136 is a sheath 123 made of a sound damping material designed to dampen resonances of the stethoscope housing 136. Electronic circuitry 135 is also mounted on damping sheath 123. Damping sheath 123 also acts as an external sound attenuator adding several dB to the sound detection device's signal to noise performance.

Fourth Stethoscope Embodiment

Figure 10:
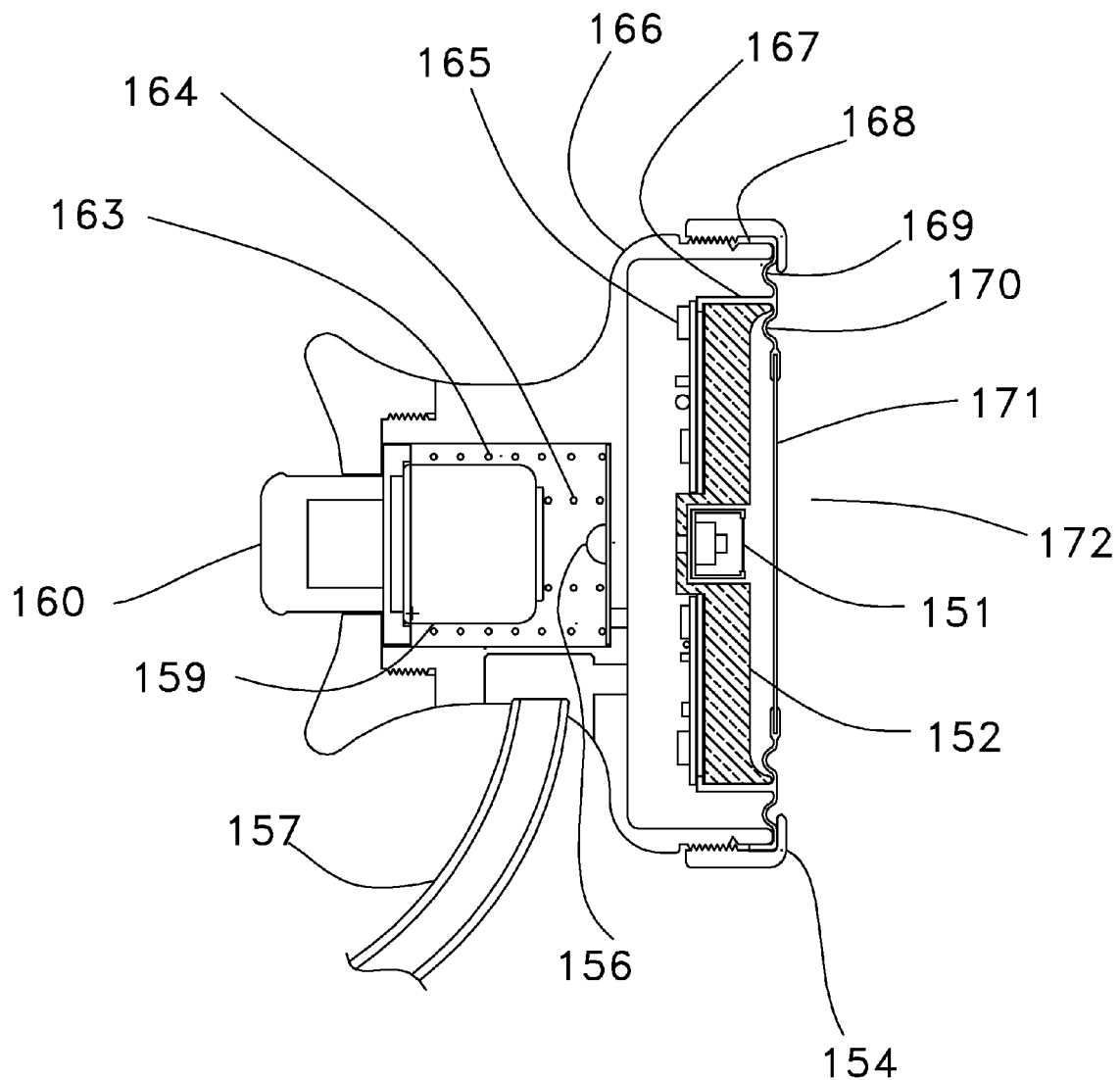
FIG. 10 is a side cross-sectional view of an embodiment of the present invention in which an electronic amplifier assembly is mounted to the floating mass.

FIG. 10 is a side cross-sectional view of an embodiment of the present invention in which an electronic amplifier assembly (165) is mounted to a floating mass (152). Electronic stethoscope chest piece 172 of FIG. 10 includes sound transducer 151 (which is typically a miniature microphone) mounted to floating mass 152. Mass 152 is mounted to specially molded diaphragm assembly 167-171, with mass 152 held in cup-like molding extension 167 of assembly 167-171 by pressure of fit. Diaphragm assembly 167-171 is mounted in chest piece housing 166 with rim portion 168 of assembly 167-171 clamped between clamp ring 154 and housing 166. In variations on the FIG. 10 embodiment, mass 152 is mounted to extension 167 by glue or is fastened to the diaphragm assembly by any other suitable means.

Diaphragm assembly 167-171 comprises thin, relatively stiff central membrane 171, rim portion 168, and annular convolutions 169 and 170, as well as extension cup 167. As shown in FIG. 10, extension cup 167 is molded so as to extend in the proximal direction from the approximate midpoint of the annular convolutions 169 and 170. The design of FIG. 10 allows diaphragm membrane 171 to move (e.g., vibrate) with respect to mass 152, while mass 152 (held in extension cup 167), diaphragm portion 171, and each other portion of the diaphragm assembly in contact with the patient's skin move freely with respect to housing 166.

When chest piece 172's distal face (the right face in FIG. 10) is placed against a patient's skin, both diaphragm portion 171 and mass 152 freely float on the skin while body 166 and clamp ring 154 are isolated somewhat from diaphragm portion 171 and mass 152 and thus from microphone 151 by the annular convolutions 169 and 170. This results in a natural improvement in the signal to noise performance of the stethoscope. Although two annular convolutions 169 and 170 are shown, more or less than two can be used in other embodiments.

Electronic stethoscope chest piece 172 also includes electronic amplifier assembly 165 and a power source 159, which is typically but not necessarily a battery. Amplified signals indicative of the microphone output are sent from amplifier 165 along wires through stethoscope tube 157 to output sound transducers, which are typically headphones (not shown) located at the stethoscope head piece (not shown) connected to stethoscope tube 157.

In chest piece 172, amplifier assembly 165 is mounted on mass 152. The advantage of this is that the connections to microphone 151 are very short which adds additional noise reduction, including by reducing or eliminating the coupling of noise vibrations directly to the microphone through the connection wires. Amplifier assembly 165 is typically rigidly bonded to mass 152 so that it does not contribute any vibration noise. In other implementations, electronic amplifier assembly 165 is glued or fastened by any other suitable means to mass 152.

Momentary push button switch 160 can be actuated to overcome opposing force exerted thereon by springs 163 and 164 to push battery 159 against contact 156, thus turning the stethoscope on when auscultation is desired. The described switching technique is only for example. There are numerous switching methods available to those of ordinary skill in the art which can be used in alternative embodiments of the inventive device.

Fifth Stethoscope Embodiment

Figure 11:
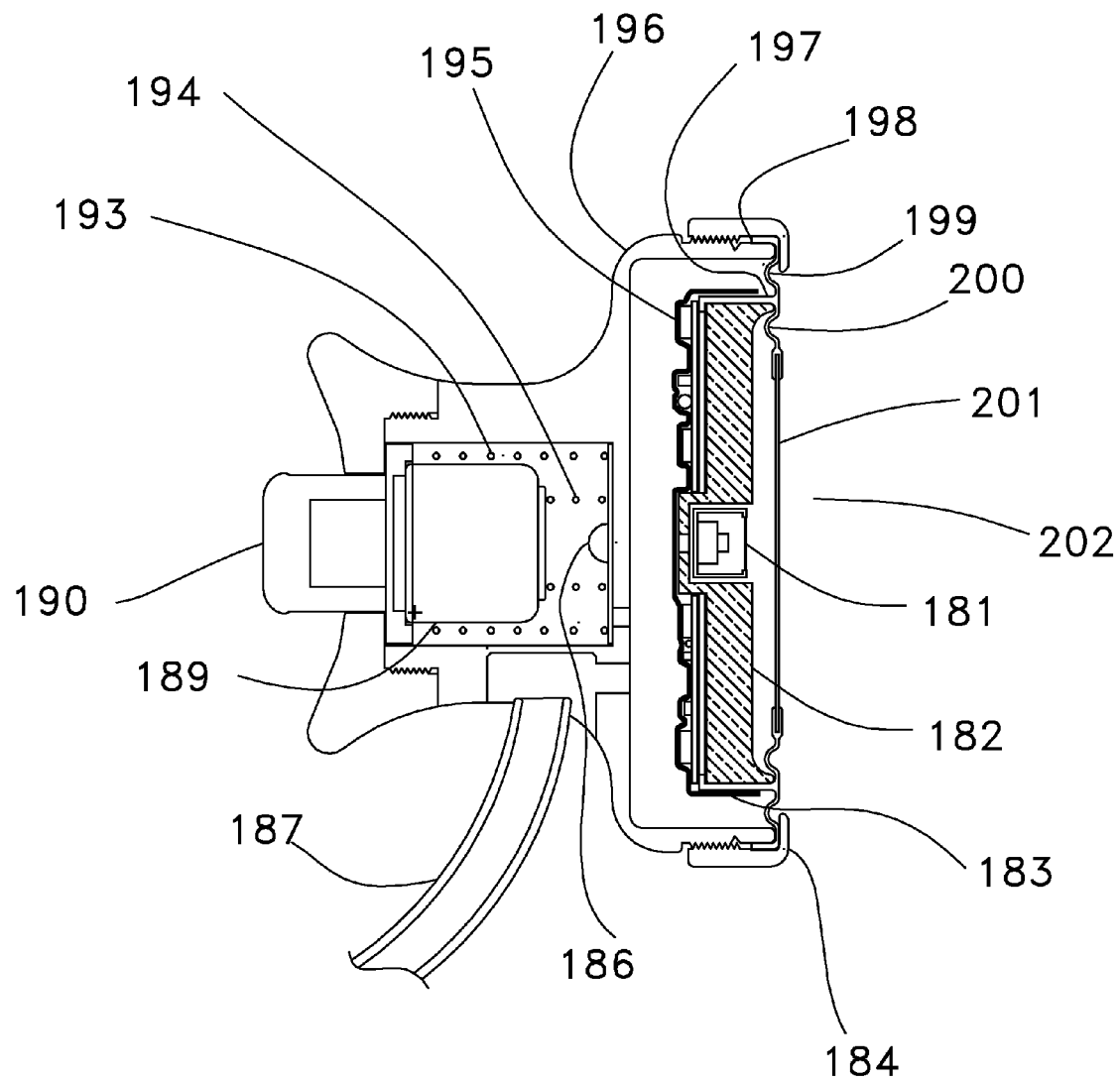
FIG. 11 is a side cross-sectional view of an embodiment of the present invention in which an acoustically damped electronic amplifier assembly is mounted to the floating mass.

FIG. 11 is a side cross-sectional view of an embodiment of the present invention in which an electronic amplifier assembly (195) is mounted to a floating mass (182) and sheathed with sound damping material (183). Electronic stethoscope chest piece 202 of FIG. 11 includes sound transducer 181 (typically a miniature microphone) mounted in floating mass 182. Mass 182 is mounted to specially molded diaphragm assembly 197-201. More specifically, mass 182 is held in molding extension 197 (which extends in the proximal direction from the rest of diaphragm assembly 197-201) by pressure of fit. Diaphragm assembly 197-201 is mounted in chest piece housing 196 with rim portion 198 of assembly 197-201 clamped between clamp ring 184 and housing 196. In variations on the FIG. 11 embodiment, mass 182 is mounted to extension 197 by glue or is fastened to the diaphragm assembly by any other suitable means.

Diaphragm assembly 197-201 includes a thin, relatively stiff membrane portion 201, rim portion 198, and annular convolutions 199 and 200, as well as extension 197. As shown in FIG. 11, extension cup 197 is molded from the approximate midpoint of annular convolutions 199 and 200. The design of FIG. 11 allows diaphragm membrane 201 to move (e.g., vibrate) with respect to mass 182, while mass 182 (held in extension cup 197), diaphragm portion 201, and each other portion of the diaphragm assembly in contact with the patient's skin move freely with respect to housing 196.

When chest piece 202's distal face (the right face in FIG. 11) is placed against a patient's skin, both diaphragm portion 201 and mass 182 freely float on the skin while body 196 and clamp ring 184 are isolated somewhat from diaphragm portion 201 and mass 182 and thus from microphone 181 by the annular convolutions 199 and 200. This results in a natural improvement in the signal to noise performance of the stethoscope. Although two annular convolutions 199 and 200 are shown, more or less than two can be used in other embodiments.

Electronic stethoscope chest piece 202 also includes electronic amplifier assembly 195 and power source 189 (which is typically but not necessarily a battery). Amplified signals indicative of the microphone output are sent along wires from amplifier assembly 195 through stethoscope tube 187 to output sound transducers, which are typically headphones (not shown) located at a stethoscope head piece (not shown) connected to stethoscope tube 187.

In chest piece 202, amplifier assembly 195 is mounted on mass 182. An advantage of this design is that the connections to microphone 181 are very short which adds additional noise reduction, including by reducing or eliminating the coupling of noise vibrations directly to the microphone through the connection wires. Amplifier assembly 195 is typically rigidly bonded to mass 182 so that it does not contribute any vibration noise. In other implementations, electronic amplifier assembly 195 is glued or fastened by other suitable means to mass 182.

Momentary push button switch 190 can be actuated to overcome opposing force exerted thereon by springs 193 and 194 to push battery 189 against contact 186, thus turning the stethoscope on when auscultation is desired. The described switching technique is only for example. There are numerous switching methods available to those of ordinary skill in the art which can be used in alternative embodiments of the inventive device.

To add further to the audio noise shielding, the FIG. 11 embodiment includes damping material 183 which surrounds the rear portion of mass 182, the electronic assembly 195, and at least a portion of the lip of extension cup 197. The noise shielding provided by material 183 adds significantly to the signal to noise performance of a stethoscope including the FIG. 11 assembly. Damping material 183 can but need not be a sprayed on paint or elastomer. Although only these two types of materials are mentioned, those of ordinary skill in the art will recognize that many other materials may be used to implement damping material 183.

Sixth Stethoscope Embodiment

Figure 12:
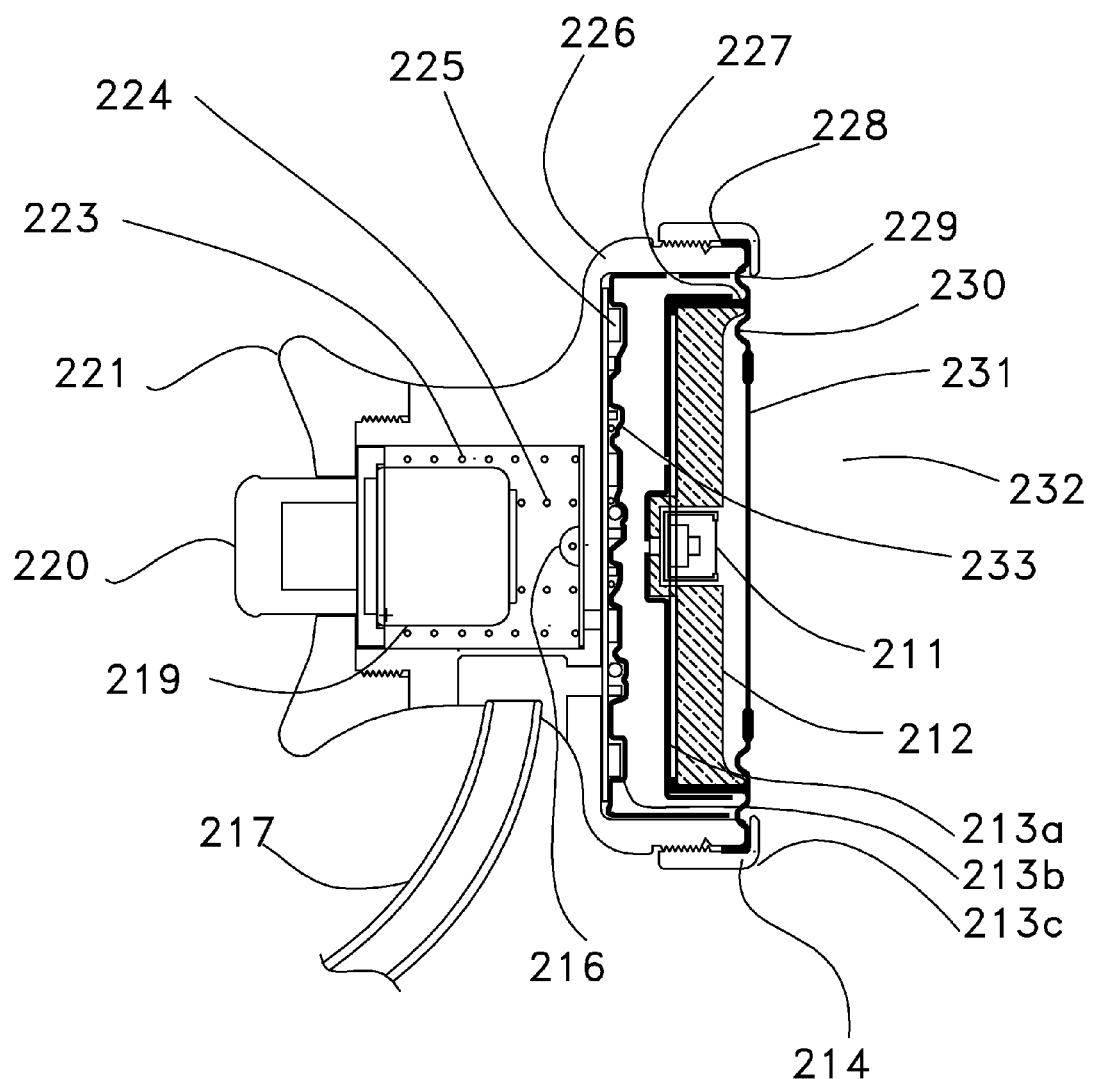
FIG. 12 is a side cross-sectional view of an embodiment of the present invention including acoustic damping material.

FIG. 12 shows a stylized half section of a sixth embodiment of electronic stethoscope chest piece (232) which is built according to the present invention. Chest piece 232 comprises sound transducer 211 (typically a miniature microphone) mounted in floating mass 212. Mass 212 is mounted to specially molded diaphragm assembly 227-231. More specifically, mass 212 is held in molding extension 227 (which extends in the proximal direction from the rest of diaphragm assembly 227-231) by pressure of fit. Diaphragm assembly 227-231 is mounted in chest piece housing 226 with rim portion 228 of assembly 227-231 clamped between clamp ring 214 and housing 226. In variations on the FIG. 12 embodiment, mass 212 is mounted to extension 227 by glue or is fastened to the diaphragm assembly by any other suitable means.

Diaphragm assembly 227-231 includes a thin, relatively stiff membrane portion 231, rim portion 228, and annular convolutions 229 and 230, as well as extension 227. As shown in FIG. 12, extension cup 227 is molded from the approximate midpoint of annular convolutions 229 and 230. The design of FIG. 12 allows diaphragm membrane 231 to move (e.g., vibrate) with respect to mass 212, while mass 212 (held in extension cup 227), diaphragm portion 231, and each other portion of the diaphragm assembly in contact with the patient's skin move freely with respect to housing 226.

When chest piece 232's distal face (the right face in FIG. 12) is placed against a patient's skin, both diaphragm portion 231 and mass 212 freely float on the skin while body 226 and clamp ring 214 are isolated somewhat from diaphragm portion 231 and mass 212 and thus from microphone 211 by the annular convolutions 229 and 230. This results in a natural improvement in the signal to noise performance of the stethoscope. Although two annular convolutions 229 and 230 are shown, more, or less can be used if desired.

Electronic stethoscope chest piece 232 also includes electronic amplifier assembly 225 and power source 219 (which is typically but not necessarily a battery). Amplified signals indicative of the microphone output are sent along wires from amplifier assembly 225 through stethoscope tube 217 to output sound transducers, which are typically headphones (not shown) located at a stethoscope head piece (not shown) connected to stethoscope tube 217. In chest piece 232, amplifier assembly 225 is mounted to housing 226.

Momentary push button switch 220 can be actuated to overcome opposing force exerted thereon by springs 223 and 224 to push battery 219 against contact 216, thus turning the stethoscope on when auscultation is desired. The described switching technique is only for example. There are numerous switching methods known to those of ordinary skill in the art which can be used in alternative embodiments of the inventive device.

To add to the audio noise shielding, there is provided damping material 213*a*, 213*b* and 213*c*. Material 213*b* coats or surrounds electronic assembly 225, material 213*a* coats or surrounds the rear portion of mass 212 (while defining a hole through which connecting wires can extend between assembly 225 and microphone 211), and material 213*c* coats or surrounds clamp ring 214. The noise shielding provided by the damping material adds significantly to the signal to noise performance of a stethoscope that includes the FIG. 12 assembly. The damping material can but need not be a sprayed on paint or elastomer. Although only these two types of material are mentioned, those of ordinary skill in the art will recognize that many other materials may be used to implement damping material 213*a*, 213*b* and 213*c*. In variations on the FIG. 12, other combinations of damping material are provided on elements of the chest piece.

Housing 226 of FIG. 12 is typically made of metal but could be made of a damping plastic composite. However, medical personnel may perceive the look and feel of a plastic composite housing as "cheap" or otherwise undesirable. To avoid such a perception, the inventive chest piece may incorporate only internal damping (not visible to medical personnel in normal use) of any of the types described herein.

Seventh Stethoscope Embodiment

Figure 13:
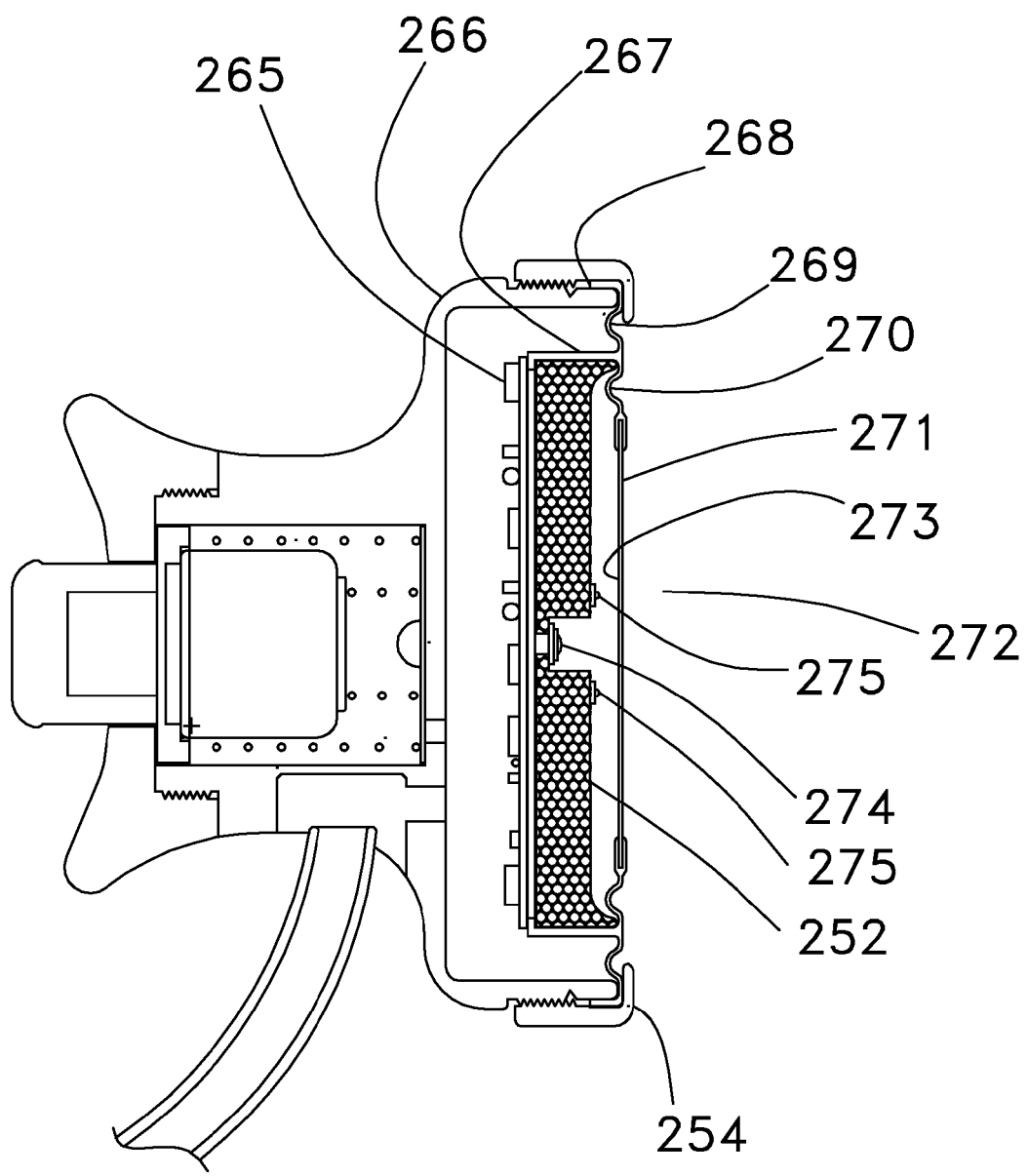
FIG. 13 is a side cross-sectional view of an embodiment of the present invention including an optical sound transducer.

FIG. 13 shows a stylized half section of a seventh embodiment electronic stethoscope chest piece which is built according to the present invention. It includes optical sensor 274 (which is a photodiode, phototransistor, or photo integrated circuit in some embodiments) mounted in floating mass 252 which is mounted to specially molded diaphragm assembly 267-271 in a chest piece housing 266. Specifically, mass 252 is held in cup-like extension molding 267 (which extends in the proximal direction (as shown) from the rest of diaphragm assembly 267-271) by pressure of fit. Alternatively, mass 252 can be mounted to the diaphragm assembly by glue or by other fastening means.

In FIG. 13, mass 252 is constructed of metal (e.g., lead or bismuth alloy) micro balls compacted loosely into a thin wall housing that is appropriately shaped. If skillfully made, it can act as an excellent dead weight which absorbs sound effectively.

Also rigidly mounted on mass 252 is at least one light emitting source 275 which is typically (but not necessarily) a light emitting diode (LED). In FIG. 13, two light emitting sources 275 are shown but a single light emitting source or more than two light emitting sources could alternatively be used. Light emitting sources 275 direct their light towards the inner (proximal) side 273 of diaphragm membrane 271.

Diaphragm assembly 267-271 includes thin, relatively stiff central membrane portion 271, rim portion 268, and annular convolutions 269 and 270, as well as extension cup 267. Inner face 273 of diaphragm membrane 271 is coated with a diffuse reflective coating. In operation, movement of diaphragm membrane 271 in sympathy with body sounds is detected by optical sensor 274 as modulations of reflected light from inner face 273.

Although acoustic transducer 274 is described herein as an optical sensor through which optical radiation propagates during use, variations on the FIG. 13 embodiment of the inventive device include an acoustic transducer similar to transducer 274 except in that non-optical electromagnetic radiation (e.g., infrared or other non-visible electromagnetic radiation) that has propagated therethrough and then reflected from a diaphragm (during use) is modulated by movement of the diaphragm in sympathy with body sounds (or other sounds) of interest that are incident on the diaphragm.

As shown in FIG. 13, extension cup 267 is molded from the approximate midpoint of annular convolutions 269 and 270. The design of FIG. 13 allows diaphragm membrane 271 to move (e.g., vibrate) with respect to mass 252, while mass 252 (held in extension cup 267), diaphragm portion 271, and each other portion of the diaphragm assembly in contact with the patient's skin move freely with respect to housing 266.

When chest piece 272's distal face (the right face in FIG. 13) is placed against a patient's skin, both diaphragm portion 271 and mass 252 freely float on the skin while body 266 and clamp ring 254 are isolated somewhat from diaphragm portion 271 and mass 252 and thus from the optical sound transducer (comprising elements 274 and 275) by the annular convolutions 269 and 270. This results in a natural improvement in the signal to noise performance of the stethoscope. Although two annular convolutions 269 and 270 are shown, more, or less can be used if desired.

Electronic stethoscope chest piece 272 also includes electronic assembly 265 and a power source (which is typically but not necessarily a battery). Electronic assembly 265 is an optoelectronic amplifier and processor, which is typically a complex device, and is preferably capable of detecting minute changes in optical power (detected by sensor 274 of the device's optical sound transducer) and translating them into audio frequency signals. Amplified signals indicative of the optical sound transducer output can be sent along wires (not shown) from amplifier assembly 265 through a stethoscope tube (shown but not labeled) to output sound transducers, which are typically headphones (not shown) located at a stethoscope head piece (not shown) connected to the stethoscope tube. In chest piece 272, amplifier assembly 265 is mounted to mass 252.

The FIG. 13 device can include a momentary push button switch that can be actuated to overcome opposing force exerted thereon by biasing springs to push a battery against an electrical contact, thus supplying power to assembly 265 and turning the stethoscope on when auscultation is desired. The described switching technique is only for example. There are numerous switching methods known to those of ordinary skill in the art which can be used in alternative embodiments of the inventive device.

Eighth Stethoscope Embodiment

Figure 14:
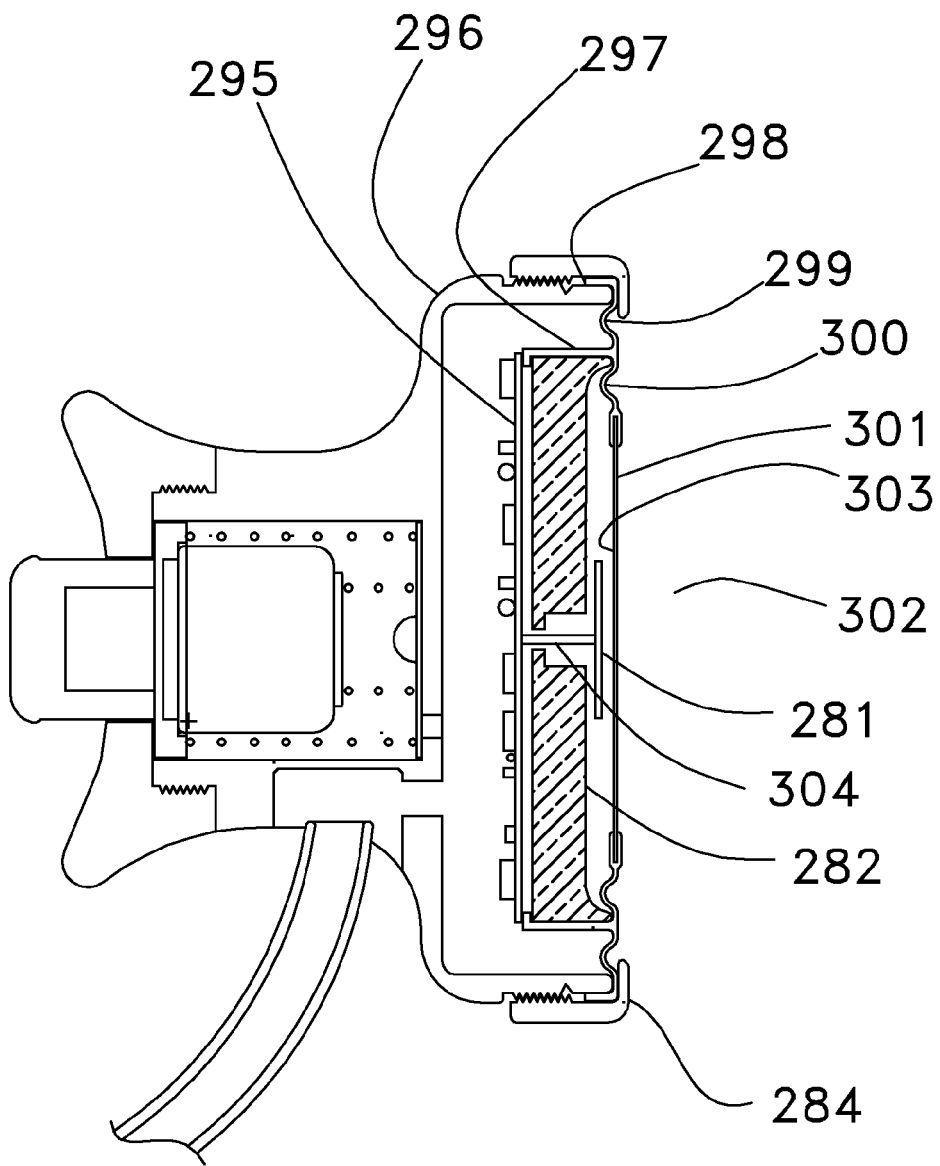
FIG. 14 is a side cross-sectional view of an embodiment of the present invention including a capacitive sound transducer.

FIG. 14 is a stylized half section of another electronic stethoscope chest piece (302) which embodies the present invention and which includes a capacitive sound transducer (identified below as capacitive sensor) coupled to an electronic assembly (295). The capacitive sensor of chest piece 302 comprises simple disk shaped plate 281 which protrudes from the printed circuit board of electronic assembly 295 at the distal end of conductive rod 304. The capacitive sensor is mounted to floating mass 282 which is mounted to specially molded diaphragm assembly 297-301 in chest piece housing 296. Specifically, mass 282 is held in cup-like extension molding 297 of the diaphragm assembly (which extends in the proximal direction as shown from the rest of diaphragm assembly) by pressure of fit. Alternatively, mass 282 can be mounted to the diaphragm assembly by glue or by other fastening means.

Diaphragm assembly 297-301 comprises a thin, relatively stiff membrane portion 301, a rim portion 298, and annular convolutions 299 and 300, as well as extension cup 297. The inner side (the left side in FIG. 14) of diaphragm membrane 301 is coated with a thin film (303) of electrically conductive material. Thin film 303 is typically grounded to housing 296 (no ground connection is shown in FIG. 14). In operation of the FIG. 14 assembly, movements of diaphragm membrane 301 in sympathy with body sounds are detected as minute capacitance changes between the face of capacitance sensor plate 281 and electrically grounded, conductive film 303 of diaphragm membrane 301.

As shown in FIG. 14, extension cup 297 is molded from the approximate midpoint of annular convolutions 299 and 300. The design of FIG. 14 allows diaphragm membrane 301 to move (e.g., vibrate) with respect to mass 282, while mass 282 (held in extension cup 297), diaphragm portion 301, and each other portion of the diaphragm assembly in contact with the patient's skin move freely with respect to housing 296.

When chest piece 302's distal face (the right face in FIG. 14) is placed against a patient's skin, both diaphragm portion 301 and mass 282 freely float on the skin while body 296 and clamp ring 284 are isolated somewhat from diaphragm portion 301 and mass 282 and thus from the capacitive sound transducer (comprising elements 281 and 304) by the annular convolutions 299 and 300. This results in a natural improvement in the signal to noise performance of a stethoscope that includes chest piece 302. Although two annular convolutions 299 and 300 are shown, more, or less can be used if desired.

Electronic assembly 295 of stethoscope chest piece 302 is preferably a capacitance to audio converter/amplifier/processor which is typically a complex device, and which is capable of detecting minute changes in capacitance and translating them into audio frequency signals. Amplified signals indicative of the capacitive sound transducer output can be sent along wires (not shown) from assembly 295 through a stethoscope tube (shown but not labeled) to output sound transducers, which are typically headphones (not shown) located at a stethoscope head piece (not shown) connected to the stethoscope tube.

Ninth Stethoscope Embodiment

Figure 15:
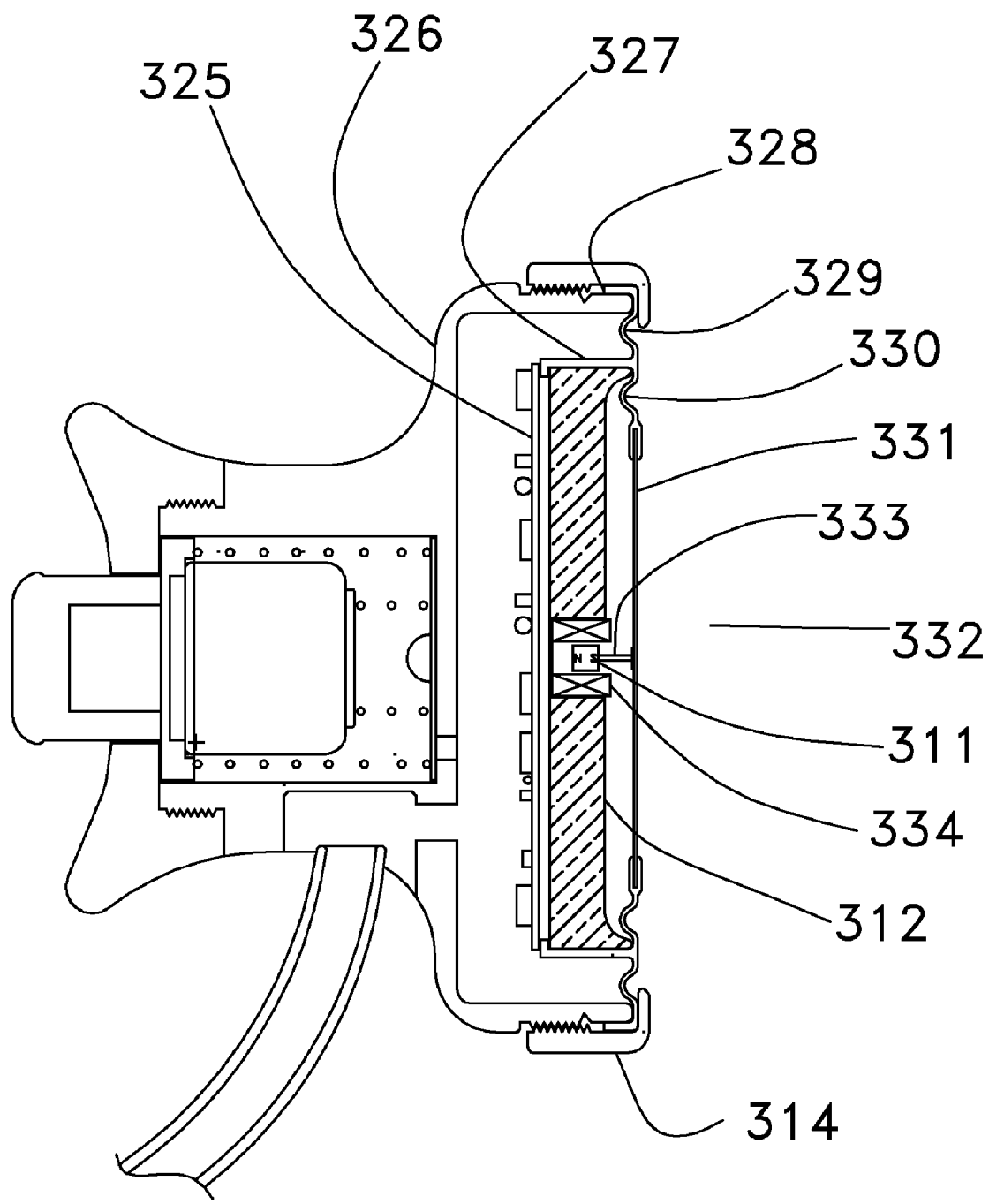
FIG. 15 is a side cross-sectional view of an embodiment of the present invention including an inductive sound transducer.

FIG. 15 is a stylized half section of another electronic stethoscope chest piece (332) which embodies the present invention and which includes an inductive sound transducer (identified below as inductive sensor) coupled to an electronic assembly (325). The inductive sensor of chest piece 332 comprises miniature multi turn coil 334 of wire rigidly mounted to floating mass 312. Mounted normal to the distal face (the back face) of diaphragm membrane 331 is a small permanent magnet 311 on a shaft 333 positioned such that the magnet 311 rides freely in the core of inductive sensor coil 334.

Floating mass 312 is mounted to specially molded diaphragm assembly 327-331 in chest piece housing 326. Specifically, mass 312 is held in cup-like extension molding 327 of the diaphragm assembly (which extends in the proximal direction as shown from the rest of diaphragm assembly) by pressure of fit. Alternatively, mass 312 can be mounted to the diaphragm assembly by glue or by other fastening means. Diaphragm assembly 327-331 comprises a thin, relatively stiff membrane portion 331, a rim portion 328, and annular convolutions 329 and 330, as well as extension cup 327. In operation of the FIG. 15 assembly, movements of diaphragm membrane 331 (and magnet 311) in sympathy with body sounds are detected as a minute electrical signal from inductive sensor coil 334 induced by moving magnet 311.

As shown in FIG. 15, extension cup 327 is molded from the approximate midpoint of annular convolutions 329 and 330. The design of FIG. 15 allows diaphragm membrane 331 to move (e.g., vibrate) with respect to mass 312, while mass 312 (held in extension cup 327), diaphragm portion 331, and each other portion of the diaphragm assembly in contact with the patient's skin move freely with respect to housing 326.

When chest piece 332's distal face (the right face in FIG. 15) is placed against a patient's skin, both diaphragm portion 331 and mass 312 freely float on the skin while body 326 and clamp ring 314 are isolated somewhat from diaphragm portion 331 and mass 312 and thus from the inductive sound transducer by the annular convolutions 329 and 330. This results in a natural improvement in the signal to noise performance of a stethoscope that includes chest piece 332. Although two annular convolutions 329 and 330 are shown, more, or less can be used if desired.

Electronic assembly 325 of stethoscope chest piece 332, mounted to the rear (proximal) face of mass 312, is preferably an amplifier/equalizer which is capable of detecting minute changes in voltage induced by the magnet 311 into inductive sensor coil 334 in response to movement of the diaphragm 331 during auscultation. Amplified signals indicative of the inductive sound transducer output can be sent along wires (not shown) from assembly 325 through a stethoscope tube (shown but not labeled) to output sound transducers, which are typically headphones (not shown) located at a stethoscope head piece (not shown) connected to the stethoscope tube.

Tenth Stethoscope Embodiment

Figure 16:
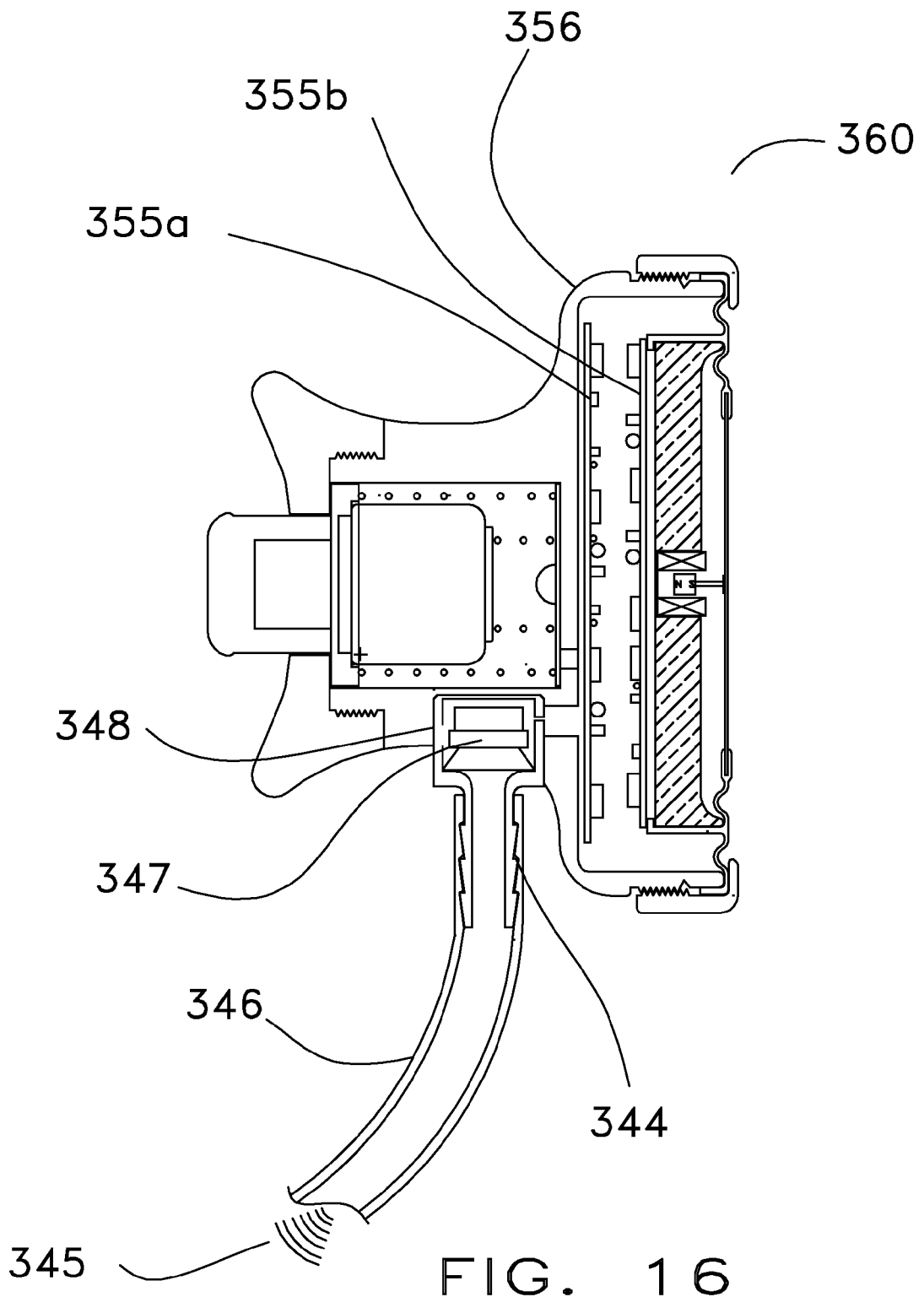
FIG. 16 is a side cross-sectional view of an embodiment of the present invention including an output sound transducer.

FIG. 16 shows a stylized half section of another embodiment of an electronic stethoscope chest piece (360) which is built according to the present invention. FIG. 16 shows a detail of a first example of placement of an output sound transducer (347) within body 356 of stethoscope chest piece 360. As shown, chest piece 360 includes an inductive sound transducer and an electronic assembly (355a and 355b) coupled and configured to generate amplified electrical signals indicative of the inductive sound transducer's output. Circuitry 335b of the electronic assembly is mounted to the floating mass of chest piece 360, and circuitry 335a of the electronic assembly is mounted to the body 356 of chest piece 360 (and coupled to circuitry 335b). Although the inductive sound transducer and electronic assembly of FIG. 16 can be identical to the inductive sound transducer and electronic assembly 325 of FIG. 15, respectively, variations on the FIG. 16 embodiment include other sound transducers (e.g., microphones or optical sound transducers) and electronic assemblies for performing any appropriate amplification and other processing of the relevant sound transducer output.

As shown in FIG. 16, amplified electrical signals from electronic assembly 355a and 355b are asserted to output sound transducer 347 which is housed in a fitting 348 including a hose barb 344 over which a standard stethoscope headpiece tube 346 can be fitted. Transducer 347 outputs acoustic waves in response to the electrical signals from the electronic assembly. Sound that is output from transducer 347 (indicated by the schematic sound representation 345) can travel up tube 346 and into a stethoscope head piece (not shown) in the same manner as does the acoustic output of a standard passive stethoscope's chest piece.

Eleventh Stethoscope Embodiment

Figure 17:
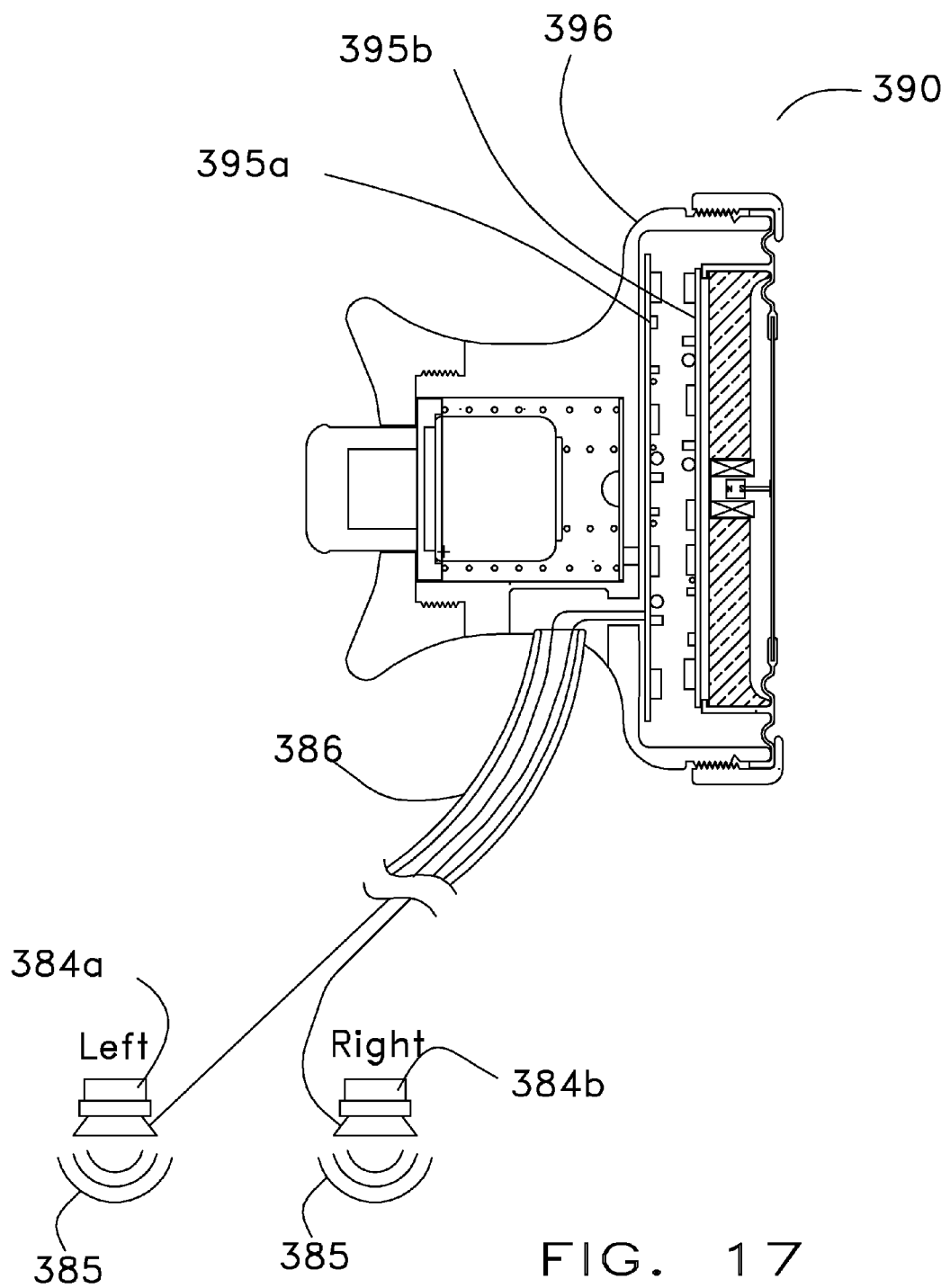
FIG. 17 is a side cross-sectional view of an embodiment of the present invention including a pair of output sound transducers, with the output sound transducers shown schematically.

FIG. 17 shows a stylized half section of an eleventh embodiment of an electronic stethoscope chest piece (390) which is built according to the present invention, and a pair of output sound transducers (384a and 384b) electrically coupled thereto. In the FIG. 17 device, output sound transducers 384a and 384b are located remotely from body 396 of stethoscope chest piece 390. As shown, chest piece 390 includes an inductive sound transducer and an electronic assembly (395a and 395b) coupled and configured to generate amplified electrical signals indicative of the inductive sound transducer's output. Circuitry 395b of the electronic assembly is mounted to the floating mass of chest piece 390, and circuitry 395a of the electronic assembly is mounted to the body 396 of chest piece 390 (and coupled to circuitry 395b). Although the inductive sound transducer and electronic assembly of FIG. 17 can be identical to the inductive sound transducer and electronic assembly 335a and 335b of FIG. 16, respectively, variations on the FIG. 17 embodiment include other sound transducers (e.g., microphones or optical sound transducers) and electronic assemblies for performing any appropriate amplification and other processing of the relevant sound transducer output.

As shown in FIG. 17, amplified electrical signals from electronic assembly 395a and 395b are asserted via wires in stethoscope headpiece tube 386 to output sound transducers 384a and 384b which are typically housed in a stethoscope head piece (not shown). Each of transducers 384a and 384b outputs acoustic waves in response to the electrical signals from the electronic assembly. Sound output from transducers 384a and 384b (indicated by the schematic sound representation 385) is audible to a physician or other user wearing the stethoscope head piece.

Twelfth Stethoscope Embodiment

Figure 18:
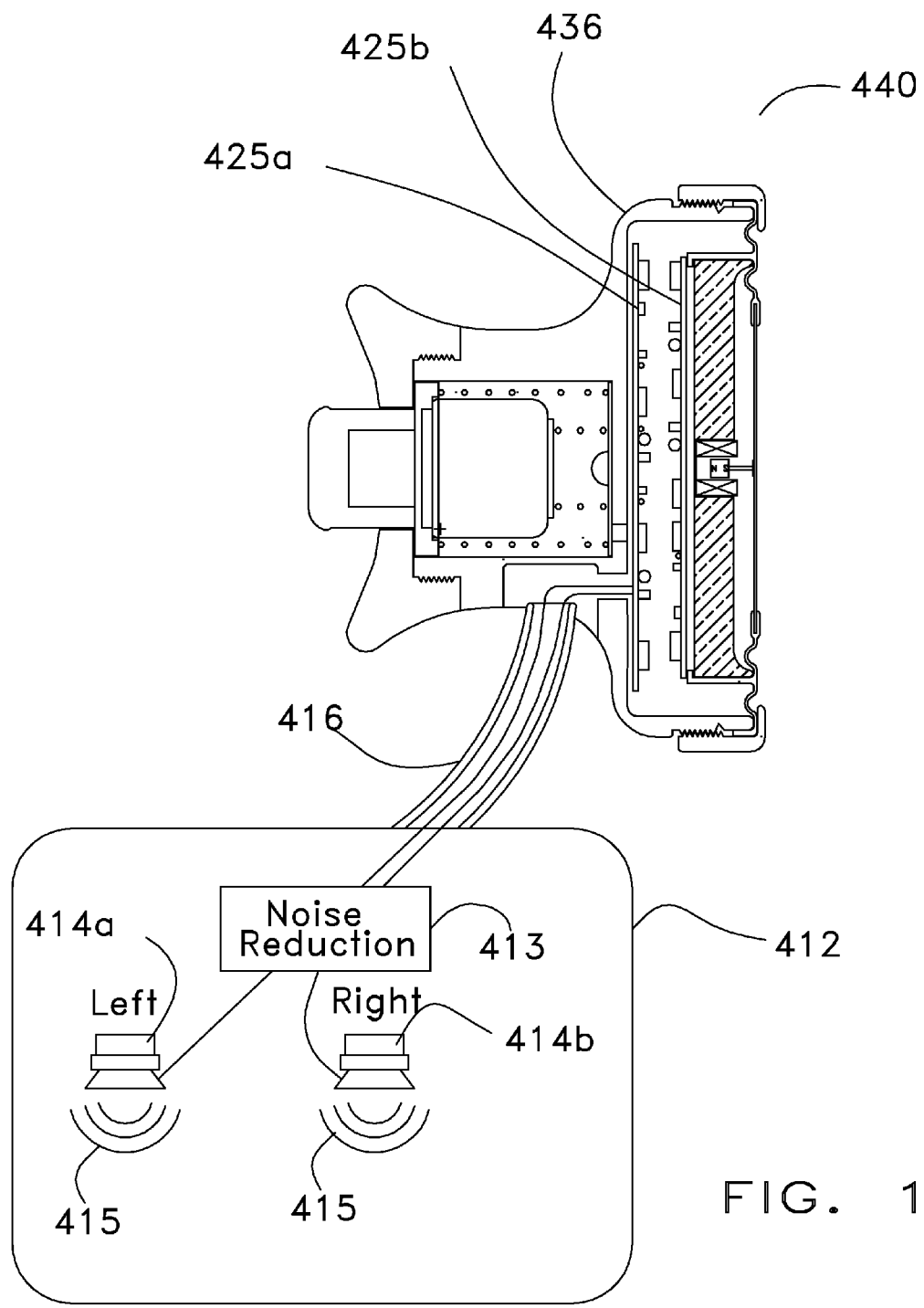
FIG. 18 is a side cross-sectional view of an embodiment of the present invention including a headset (412), shown schematically, and a chest piece (440). The headset includes a pair of output noise cancelling sound transducers.

FIG. 18 shows a stylized half section of a twelfth embodiment of an electronic stethoscope which is built according to the present invention, including a chest piece (440) and a headset (412) including a pair of output sound transducers (414a and 414b) and noise reduction circuitry 413 electrically coupled thereto. In the FIG. 18 device, circuitry 413 and output sound transducers 414a and 414b are located remotely from body 436 of stethoscope chest piece 440. As shown, chest piece 440 includes an inductive sound transducer and an electronic assembly (425a and 425b) coupled and configured to generate amplified electrical signals indicative of the inductive sound transducer's output. Circuitry 425b of the electronic assembly is mounted to the floating mass of chest piece 440, and circuitry 425a of the electronic assembly is mounted to the body 436 of chest piece 440 (and coupled to circuitry 425b). Although the inductive sound transducer and electronic assembly of FIG. 18 can be identical to the inductive sound transducer and electronic assembly 335a and 335b of FIG. 16, respectively, variations on the FIG. 18 embodiment include other sound transducers (e.g., microphones or optical sound transducers) and electronic assemblies for performing any appropriate amplification and other processing of the relevant sound transducer output.

As shown in FIG. 18, amplified electrical signals from electronic assembly 425a and 425b are asserted via wires through stethoscope headpiece tube 416 to noise reduction circuitry 413 which is typically housed (with output sound transducers 414a and 414b) in a stethoscope head piece 412 (shown schematically). Head piece 412 can be a set of ambient noise reducing headphones. Each of transducers 414a and 414b outputs acoustic waves in response to the electrical signals from circuitry 413. Circuitry 413 is configured to perform noise reduction on the electrical signals asserted thereto from electronic assembly 425a and 425b. Sound output from transducers 414a and 414b (indicated by the schematic sound representation 415) is audible to a physician or other user wearing head piece 412. This embodiment of the inventive active electronic stethoscope is expected to be useful in noisy environments (for example, in ambulances) and in many medical emergency situations.

Thirteenth Stethoscope Embodiment

FIG. 19 shows a stylized half section of an electronic stethoscope which is built according to the present invention. This embodiment includes a chest piece (472), a headset (412), and an optical transmitter and optical receiver circuit block 422 (identified in the figure as an "optical Tx/Rx" 422) which can be positioned remotely from the chest piece. Circuit block 422 is typically positioned far from chest piece 472 (e.g., with block 422 in one room and chest piece 472 in another room) during use of the device. Circuit block 422 may be included in the headset in a variation on the FIG. 19 embodiment.

Headset (412) is identical to the identically numbered headset in FIG. 18, and includes a pair of output sound transducers (414a and 414b) and noise reduction circuitry 413 electrically coupled thereto.

Chest piece 472 includes an optical acoustic transducer (comprising optical fibers 474 and 476). In operation, a light emitting source (typically but not necessarily a light emitting diode) in optical Tx/Rx block 422 transmits light into fiber 476. At least some of the light propagates out from fiber 476 and is reflected from the inner (proximal) side 473 of diaphragm membrane 471. At least some of the reflected light propagates into fiber 474, as best shown in FIG. 20 (which is a magnified view of the distal portions of optical fibers 474 and 476 in mass 452). This reflected light propagates through fiber 474 to an optical receiver portion of block 422. Block 422 is coupled and configured to receive the reflected light and to generate amplified electrical signals indicative of the optical acoustic transducer's output in response thereto. Optical Tx/Rx circuit block 422 typically contains optical to audio conversion circuitry (e.g., of a type well known in the art) that produces electrical signals in accordance to detected light variations. In operation, reflected electromagnetic radiation that propagates to block 422 will be influenced by movement of diaphragm 471. This movement will result in a change in the intensity of the radiation received at block 422, and also in a phase change in the radiation received at block 422 if high frequency optical signals are used. Both or either of these effects can be detected by optical to audio conversion circuitry in block 422.

The filled arrows in FIG. 20 indicate transmitted light energy from an optical transmitter Tx within block 422, while the unfilled arrows in FIG. 20 indicate reflected light energy on its way to an optical receiver Rx within block 422.

Chest piece 472 of FIG. 19 is completely non-powered stethoscope chest piece whose design makes it useful in MRI (magnetic resonance imaging) environments and other environments in which hyper-intense magnetic fields (or other intense electromagnetic fields) and/or various microwave emanations are present. Chest piece 472 is typically constructed of non-magnetic and non-metallic materials. For example, housing 466 can be made of a plastic such as, for example, an acrylic material, or ABS or PVC plastic. Other non-plastic materials could also be used. Floating mass 452 can be formed of a high density polymer, as described elsewhere herein. Housing 466 preferably has a simple shape (e.g., that of a small hockey puck) and is designed to be taped to the patient's body.

The length of each of optical fibers 476 and 474 is almost unlimited, so that the FIG. 19 apparatus can be implemented with circuit block 422 and headset 412 far from chest piece 472 during use. For example, circuit block 422 and headset 412 (and the physician wearing the head piece) can be located in a different room than chest piece 472 and the patient whose body sounds are to be detected. In practical use, an MRI machine is extremely noisy, so that a stethoscope designed in accordance with FIGS. 19-20 might not be used routinely during MRI procedures but rather as a pre-procedure and post-procedure monitoring device. Other possible uses of such a stethoscope are in ambulatory situations, such as ground vehicle or airborne vehicle patient monitoring.

Floating mass 452 is mounted to specially molded diaphragm assembly 467-471 in chest piece housing 466. Specifically, mass 452 is held in cup-like extension molding 467 of the diaphragm assembly (which extends in the proximal direction as shown from the rest of diaphragm assembly) by pressure of fit. Alternatively, mass 452 can be mounted to the diaphragm assembly by glue or by other fastening means.

Optical fibers 474 and 476 are mounted at their distal ends to mass 452, and are coupled at their proximal ends to optical Tx/Rx circuit block 422. Circuit block 422 is remote from chest piece 472.

Diaphragm assembly 467-471 includes thin, relatively stiff central membrane portion 471, rim portion 468, and flexible annular convolutions 469 and 470, as well as extension cup 467. Inner face 473 of diaphragm membrane 471 is preferably coated with a diffuse reflective coating. In operation of the FIG. 19 device, movement of diaphragm membrane 471 in sympathy with body sounds is detected by the optical sensor as modulations of reflected light from inner face 473.

As shown in FIG. 19, extension cup 467 is molded from the approximate midpoint of annular convolutions 469 and 470. The design of FIG. 19 allows diaphragm membrane 471 to move (e.g., vibrate) with respect to mass 452, while mass 452 (held in extension cup 467), diaphragm portion 471, and each other portion of the diaphragm assembly in contact with the patient's skin move freely with respect to housing 466.

When chest piece 472's distal face (the right face in FIG. 19) is placed against a patient's skin, both diaphragm portion 471 and mass 452 freely float on the skin while body 466 and clamp ring 454 are isolated somewhat from diaphragm portion 471 and mass 452, and thus from the optical acoustic transducer, by the annular convolutions 469 and 470.

Although the optical acoustic transducer described with reference to FIGS. 19 and 20 is an optical sensor through which optical radiation propagates during use, in variations on the embodiment of FIGS. 19-20, the inventive device includes an acoustic transducer similar to the transducer of FIGS. 19-20 except in that non-optical electromagnetic radiation (e.g., infrared or other non-visible electromagnetic radiation) that has propagated therethrough and then reflected from a diaphragm (during use) is modulated by movement of the diaphragm in sympathy with body sounds (or other sounds) of interest that are incident on the diaphragm. Additionally, no collimating lenses are shown in front of above-mentioned optical fibers. Such lenses may be included in variations on the above-described embodiments.

As shown in FIG. 19, amplified electrical signals from optical Tx/Rx block 422 are electrically communicated (e.g., asserted via wires) to noise reduction circuitry 413 which is housed (with output sound transducers 414*a* and 414*b*) in stethoscope headset 412. Thus, headset 412 is a noise isolated headset. For example, headset 412 can be implemented as a set of ambient noise reducing headphones. Each of transducers 414*a* and 414*b* outputs acoustic waves in response to the electrical signals from circuitry 413. Circuitry 413 is configured to perform noise reduction on the electrical signals asserted thereto from block 422. Sound output from transducers 414*a* and 414*b* (indicated by the schematic sound representation 415) is audible to a physician or other user wearing head piece 412. Although a noise reducing headset example is described, head piece 412 can be replaced by a conventional headset or even a loudspeaker positioned in a location remote from chest piece 472 in alternative embodiments of the invention.

It should be appreciated that although FIGS. 19-24 do not show optical connectors from optical Tx/Rx blocks 422, 522 and 622, practical implementations of these embodiments would include such connectors. Optical connectors are well known in the art and come in many varieties.

Fourteenth Stethoscope Embodiment

FIG. 21 shows a stylized half section of an electronic stethoscope which is built according to the present invention, including a chest piece (572), a headset (412), and an optical transmitter and optical receiver circuit block 522 (identified in the figure as an "optical Tx/Rx" 522) which can be positioned remotely from the chest piece. Circuit block 522 is typically positioned far from chest piece 572 (e.g., with block 522 in one room and chest piece 572 in another room) during use of the device. Circuit block 522 may be included in the headset in a variation on the FIG. 21 embodiment.

Headset (412) is identical to the identically numbered headset in FIG. 18, and includes a pair of output sound transducers (414*a* and 414*b*) and noise reduction circuitry 413 electrically coupled thereto.

Chest piece 572 includes an optical acoustic transducer (comprising optical fiber 574). In operation, a light emitting source (typically but not necessarily a light emitting diode) in optical Tx/Rx block 522 transmits light into fiber 574 At least some of the light propagates out from fiber 574 and is reflected from the inner (proximal) face 573 of diaphragm membrane 571. At least some of the reflected light propagates back into fiber 574, as best shown in FIG. 22 (which is a magnified view of the distal portion of optical fiber 574 in mass 552). This reflected light propagates through fiber 574 to an optical receiver portion of block 522. Block 522 is coupled and configured to receive the reflected light and to generate amplified electrical signals indicative of the optical acoustic transducer's output in response thereto. Block 522 contains an optical splitter for separating the incoming and outgoing optical signals, and optical to audio conversion circuitry that produces electrical signals in accordance to detected light variations (as indicated by the incoming optical signal from fiber 574). In operation, reflected electromagnetic radiation that propagates from diaphragm 571 to block 522 will be influenced by movement of diaphragm 571. This movement will result in a change in the intensity of the radiation received at block 522, and also in a phase change in the radiation received at block 522 if high frequency optical signals are used. Both or either of these effects can be detected by the optical to audio conversion circuitry in block 522.

The filled arrows in FIG. 22 indicate transmitted light energy from an optical transmitter Tx within block 522, while the unfilled arrows in FIG. 22 indicate reflected light energy on its way to an optical receiver Rx within block 522.

Floating mass 552 is mounted to specially molded diaphragm assembly 567-571 in chest piece housing 566. Specifically, mass 552 is held in cup-like extension molding 567 of the diaphragm assembly (which extends in the proximal direction as shown from the rest of diaphragm assembly) by pressure of fit. Alternatively, mass 552 can be mounted to the diaphragm assembly by glue or by other fastening means.

Optical fiber 574 is mounted at its distal end to mass 552, and coupled at its proximal end to optical Tx/Rx circuit block 522. Circuit block 522 is remote from chest piece 572.

Diaphragm assembly 567-571 includes thin, relatively stiff central membrane portion 571, rim portion 568, and flexible annular convolutions 569 and 570, as well as extension cup 567. Inner face 573 of diaphragm membrane 571 is preferably coated with a diffuse reflective coating. In operation of the FIG. 21 device, movement of diaphragm membrane 571 in sympathy with body sounds is detected by the optical sensor as modulations of reflected light from inner face 573.

As shown in FIG. 21, extension cup 567 is molded from the approximate midpoint of annular convolutions 569 and 570. The design of FIG. 21 allows diaphragm membrane 571 to move (e.g., vibrate) with respect to mass 552, while mass 552 (held in extension cup 567), diaphragm portion 571, and each other portion of the diaphragm assembly in contact with the patient's skin move freely with respect to housing 566.

When chest piece 572's distal face (the right face in FIG. 21) is placed against a patient's skin, both diaphragm portion 571 and mass 552 freely float on the skin while body 566 and clamp ring 554 are isolated somewhat from diaphragm portion 571 and mass 552, and thus from the optical acoustic transducer, by the annular convolutions 569 and 570.

Although the optical acoustic transducer described with reference to FIGS. 21 and 22 is an optical sensor through which optical radiation propagates during use, in variations on the embodiment of FIGS. 21-22, the inventive device includes an acoustic transducer similar to the transducer of FIGS. 21-22 except in that non-optical electromagnetic radiation (e.g., infrared or other non-visible electromagnetic radiation) that has propagated therethrough and then reflected from a diaphragm (during use) is modulated by movement of the diaphragm in sympathy with body sounds (or other sounds) of interest that are incident on the diaphragm. Additionally, no collimating lens is shown in front of above-mentioned optical fiber. Such a lens may be included in variations on the above-described embodiments.

As shown in FIG. 21, amplified electrical signals from optical Tx/Rx block 522 are electrically communicated (e.g., asserted via wires) to noise reduction circuitry 413 which is housed (with output sound transducers 414*a* and 414*b*) in stethoscope headset 412. Thus, headset 412 is a noise isolated headset. For example, headset 412 can be implemented as a set of ambient noise reducing headphones. Each of transducers 414*a* and 414*b* outputs acoustic waves in response to the electrical signals from circuitry 413. Circuitry 413 is configured to perform noise reduction on the electrical signals asserted thereto from block 522. Sound output from transducers 414a and 414b (indicated by the schematic sound representation 415) is audible to a physician or other user wearing headset 412. Although a noise reducing headset example is described, head piece 412 can be replaced by a conventional headset (lacking noise reduction circuitry) or even a loudspeaker positioned in a location remote from chest piece 572 during use, in alternative embodiments of the invention.

Chest piece 572 of FIG. 21 is completely non-powered stethoscope chest piece which is designed primarily for use in MRI environments and other environments in which hyperintense magnetic fields and various microwave emanations are present. Chest piece 572 is typically constructed of non-magnetic and non-metallic materials. For example, housing 566 can be made of a plastic such as, for example, an acrylic material, or ABS or PVC plastic. Other non-plastic materials could also be used. Floating mass 552 can be formed of a high density polymer, as was previously described. Housing 566 preferably has a simple shape (e.g., that of a small hockey puck) and is designed to be taped to the patient's body.

The length of optical fiber 574 is almost unlimited. In practical use, an MRI machine is extremely noisy, so that a stethoscope designed in accordance with FIGS. 21-22 might not be used routinely during MRI procedures but rather as a pre-procedure and post-procedure monitoring device. Other possible uses of such a stethoscope are in ambulatory situations, such as ground vehicle or airborne vehicle patient monitoring.

Fifteenth Stethoscope Embodiment

Figure 23:
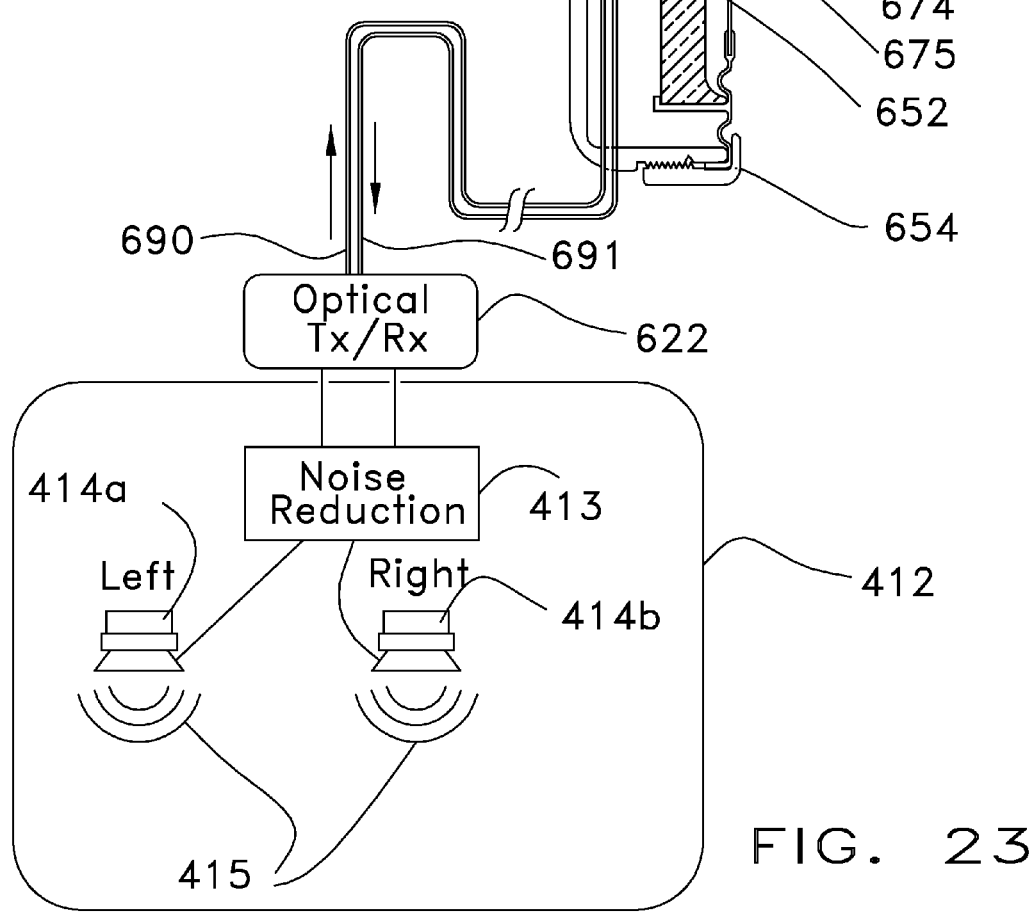
FIG. 23 is a side cross-sectional view of another embodiment of the inventive stethoscope including a non-powered optical chest piece (including an optical sound transducer) and a headset (412) including noise canceling output sound transducers. The stethoscope also includes optical transmitter and receiver circuitry which is typically located remotely from the chest piece (e.g., in a different room than the chest piece) during use, and is configured to receive and convert the output of the chest piece into an electrical signal for assertion to noise reduction circuitry in the headset.

FIG. 23 is a stylized half section of an electronic stethoscope which is built according to the present invention, including a chest piece (672), a headset (412), and an optical transmitter and optical receiver circuit block 622 (identified in the figure as an "optical Tx/Rx" 622) which can be positioned remotely from the chest piece. Circuit block 622 is typically positioned far from chest piece 672 (e.g., with block 622 in one room and chest piece 672 in another room) during use of the device. Circuit block 622 may be included in the headset in a variation on the FIG. 23 embodiment.

Headset (412) is identical to the identically numbered headset in FIG. 18, and includes a pair of output sound transducers (414a and 414b) and noise reduction circuitry 413 electrically coupled thereto.

Chest piece 672 includes an optical acoustic transducer comprising optical fiber 674, which has a looped section adjacent to diaphragm membrane 671. In operation, a light emitting source (typically but not necessarily a light emitting diode) in optical Tx/Rx block 622 transmits light into fiber 674. Light emitted from block 622 propagates up a first optical fiber section 690 of fiber 674, travels its circuit through the coiled loop portion of fiber 674, and then propagates back to block 622 through fiber section 691 of fiber 674.

Figure 24:
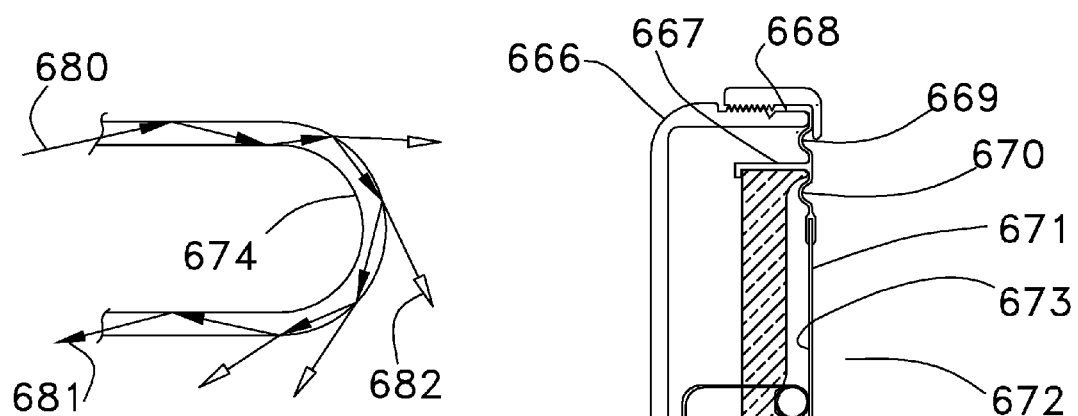
FIG. 24 is an enlarged detail of the non-powered optical chest piece of FIG. 23.

The manner in which the optical transducer operates is shown more clearly in FIG. 24, which is a magnified view showing only a half turn of the coiled loop portion of fiber 674. For clarity, FIG. 24 does not show diaphragm membrane 671. Filled arrows 680 in FIG. 24 indicate transmitted light energy from the optical transmitter Tx in block 622, and filled arrows 681 indicate light energy that has propagated through the coiled loop portion and is propagating back to an optical receiver Rx in block 622. Unfilled arrows 682 indicate light energy that escapes from fiber 674 (through fiber 674's sidewall) during propagation in the coiled loop portion of fiber 674 due to diffractive light angle changes in the coiled fiber loop portion in response to movement of membrane 671. Movement of membrane 671 in sympathy with sounds impinging thereon causes minute deformation of the coiled loop portion of fiber 674, which in turn causes the modulations of the optical signal received at the optical receiver in block 622.

Some of the light that has propagated into fiber 674 from the transmitter in block 622 propagates back through fiber 674 to an optical receiver portion of block 622. Block 622 is coupled and configured to receive this light and to generate amplified electrical signals indicative of the optical acoustic transducer's output in response thereto. Specifically, block 622 contains optical to audio conversion circuitry that produces electrical signals in accordance to detected light variations (as indicated by the incoming optical signal from fiber 674). In operation, electromagnetic radiation that propagates from block 622, through the loop portion of fiber 674 adjacent to diaphragm membrane 671, and back to block 622 will be influenced by movement of diaphragm 671. This movement results in a change in the intensity of the radiation received at block 622, and also in a phase change in the radiation received at block 622 if high frequency optical signals are used. Either or both of these effects can be detected by the optical to audio conversion circuitry in block 622.

Floating mass 652 is mounted to specially molded diaphragm assembly 667-671 in chest piece housing 666. Specifically, mass 652 is held in cup-like extension molding 667 of the diaphragm assembly (which extends in the proximal direction as shown from the rest of diaphragm assembly) by pressure of fit. Alternatively, mass 652 can be mounted to the diaphragm assembly by glue or by other fastening means.

Optical fiber 674 is mounted to mass 652 (i.e., portions of fiber 674 adjacent to fiber 674's coiled loop portion are mounted to mass 652, as shown in FIG. 23). Both ends of fiber 674 are coupled to optical Tx/Rx circuit block 622. Circuit block 622 is remote from chest piece 672.

Diaphragm assembly 667-671 includes thin, relatively stiff central membrane portion 671, rim portion 668, and flexible annular convolutions 669 and 670, as well as extension cup 667. The coiled loop portion of fiber 674 is biased against (or mounted to) inner face 673 of diaphragm membrane 671 so as to remain in contact with face 673 during operation. Typically, the coiled loop portion (which is a transducer coil portion) of fiber 674 is bonded to mass 652 and to face 673 of diaphragm membrane 671. In operation of the FIG. 23 device, movement of diaphragm membrane 671 in sympathy with body sounds is detected by the optical sensor as modulations of the electromagnetic radiation that does not escape from the coiled loop portion of fiber 674 (through fiber 674's sidewall) as it propagates through the coiled loop portion of fiber 674, and instead propagates through fiber 674 from the transmitter in block 622 back to the receiver in block 622.

As shown in FIG. 23, extension cup 667 is molded from the approximate midpoint of annular convolutions 669 and 670. The design of FIG. 24 allows diaphragm membrane 671 to move (e.g., vibrate) with respect to mass 652, while mass 652 (held in extension cup 667), diaphragm portion 671, and each other portion of the diaphragm assembly in contact with the patient's skin move freely with respect to housing 666.

When chest piece 672's distal face (the right face in FIG. 24) is placed against a patient's skin, both diaphragm portion 671 and mass 652 freely float on the skin while body 666 and clamp ring 654 are isolated somewhat from diaphragm portion 671 and mass 652, and thus from the optical acoustic transducer, by the annular convolutions 669 and 670.

Although the optical acoustic transducer described with reference to FIGS. 23 and 24 is an optical sensor through which optical radiation propagates during use, in variations on the embodiment of FIGS. 23-24, the inventive device includes an acoustic transducer similar to the transducer of FIGS. 23-24 except in that non-optical electromagnetic radiation (e.g., infrared or other non-visible electromagnetic radiation) that has propagated therethrough is modulated by movement of a diaphragm in sympathy with sounds (e.g., body sounds) of interest that are incident on the diaphragm.

As shown in FIG. 23, amplified electrical signals from optical Tx/Rx block 622 are electrically communicated (e.g., asserted via wires) to noise reduction circuitry 413 which is housed (with output sound transducers 414a and 414b) in stethoscope headset 412. Thus, headset 412 is a noise isolated headset (e.g., a set of ambient noise reducing headphones). Circuitry 413 is configured to perform noise reduction on the electrical signals asserted thereto from block 622. Each of transducers 414a and 414b produces an acoustic output in response to the electrical signals from circuitry 413. The sound output from transducers 414a and 414b (indicated by the schematic sound representation 415) is audible to a physician or other user wearing headset 412. Although a noise reducing headset example is described, headset 412 can be replaced by a conventional headset (lacking noise reduction circuitry) or even a loudspeaker positioned in a location remote from chest piece 672 during use, in alternative embodiments of the invention.

Chest piece 672 of FIG. 23 is completely non-powered stethoscope chest piece which is designed primarily for use in MRI environments and other environments in which hyper-intense magnetic fields and various microwave emanations are present. Chest piece 672 is typically constructed of non-magnetic and non-metallic materials. For example, housing 666 can be made of a plastic such as, for example, an acrylic material, or ABS or PVC plastic. Other non-plastic materials could also be used. Floating mass 652 can be formed of a high density polymer, as was previously described. Housing 666 preferably has a simple shape (e.g., that of a small hockey puck) and is designed to be taped to the patient's body.

The length of optical fiber 674 is almost unlimited. In practical use, an MRI machine is extremely noisy, so that a stethoscope designed in accordance with FIGS. 23-24 might not be used routinely during MRI procedures but rather as a pre-procedure and post-procedure monitoring device. Other possible uses of such a stethoscope are in ambulatory situations, such as ground vehicle or airborne vehicle patient monitoring.

The sensitivity to movement of the coil portion of optical fiber 674 is a function of the number of turns. The optical fiber used in typical embodiments can be of very small diameter (less than 0.008") so its relative stiffness is low, and so that the coil portion can have many turns.

High ambient sounds that impinge upon the human body, for example in an emergency ambulance or aircraft, will cause body surface acoustic waves to appear in sympathy with those sounds. These surface acoustic waves can propagate as noise to the center region of a stethoscope chest piece's diaphragm membrane (where an acoustic transducer is typically located) when the chest piece is placed against the body for auscultation. This can cause severe interference, so that the surface wave noise needs to be suppressed. In non-stethoscope applications in which sounds in an object (other than a human or animal body) are to be detected using a device resting on a surface of the object, acoustic surface waves that propagate along the object's surface (but have not originated from within the object) can also cause severe interference so that the surface wave noise needs to be suppressed.

The sixteenth and seventeenth embodiments (to be described below) are designed to achieve such surface noise suppression.

Sixteenth Embodiment

A High Ambient Noise Rejecting Stethoscope or Sound Detection Device

Figure 25:
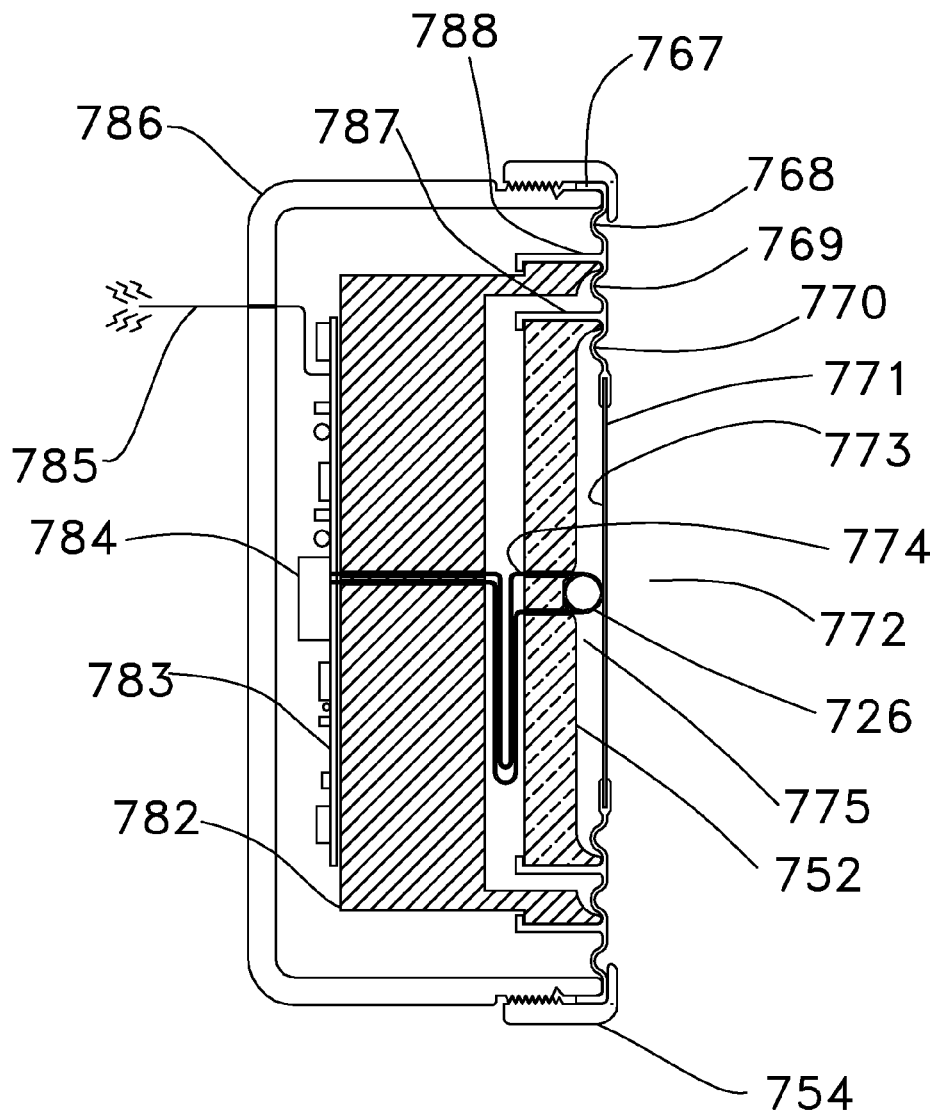
FIG. 25 is a side cross-sectional view of an embodiment of the inventive sound pickup device which can be used for many applications including as a stethoscope chest piece, and which includes two floating masses (752 and 782) and an optical transducer. The optical transducer converts sound of interest (e.g., body sounds) into optical waves and converts the optical waves into an electromagnetic signal that is transmitted wirelessly via antenna 785.

FIG. 25 is a stylized half section of an embodiment of an electronic, high ambient noise rejecting, sound detection device (772) which can function as a stethoscope chest piece and is built according to the present invention. Device 772 comprises an optical fiber 774 having a section that is wound into a transducer coil portion 726 (the coil section between floating mass 752 and diaphragm membrane 771 which has circular appearance as viewed in FIG. 25). Fiber 774's transducer coil portion 726 (and/or at least one portion of fiber 774 adjacent thereto) is mounted to floating mass 752, and the transducer coil portion 726 biased against (or mounted to) inner face 773 of diaphragm membrane 771 so as to remain in contact with face 773 as shown in FIG. 25 during operation. Typically, the transducer coil portion 726 of optical fiber 774 is bonded to both mass 752 and face 773.

In operation of the FIG. 25 device, movement of diaphragm membrane 771 in sympathy with acoustic waves of interest (e.g., body sounds) is detected by an optical sensor (the transducer coil portion 726 of fiber 774) as modulations of light (or other electromagnetic radiation) transmitted through the optical sensor. The electromagnetic radiation transmitted through the optical sensor is electromagnetic energy that does not escape through the optical sensor's sidewall and instead propagates through fiber 774 from a transmitter in optical transmitter/receiver block 784 through the optical sensor and back to an optical receiver in block 784. Movement of membrane 771 in sympathy with sounds impinging thereon causes minute deformation of the transducer coil portion 726 of optical fiber 774, which in turn causes the modulations of the optical signal received at the optical receiver in block 784.

The FIG. 25 assembly includes two floating masses: floating mass 752 and floating mass 782. Each floating mass is mounted to specially molded diaphragm assembly 767-788 in housing 786 (which functions as a chest piece housing when the FIG. 25 assembly functions as a stethoscope chest piece). As shown, floating mass 752 is mounted to diaphragm assembly 767-788 in the sense that it is held in cup-like extension molding 787 of the diaphragm assembly (which extends in the proximal direction as shown from the rest of diaphragm assembly) by pressure of fit. As shown, floating mass 782 (which is preferably larger than mass 752) is mounted to diaphragm assembly 767-788 in the sense that it is held in cup-like extension molding 788 of the diaphragm assembly (which extends in the proximal direction as shown from the rest of diaphragm assembly) by pressure of fit. Alternatively, one or both of mass 752 and mass 782 is mounted to the diaphragm assembly by glue or other mounting means.

Both ends of fiber 774 are coupled to optical transmitter/receiver (Tx/Rx) block 784. Optical Tx/Rx block 784, and the other components of electronics package 783 are mounted to the back face of mass 782 as shown. Block 784 is coupled and configured to perform the same functions as do the transmitter and receiver of block 622 of FIG. 25.

Other components of electronic package 783 are optical to audio conversion circuitry (e.g., of a type well known in the art), antenna 785, and a Radio Frequency transmitter coupled to antenna 785. The optical to audio conversion circuitry is coupled and configured to produce electrical signals in response to the optical signal received at the receiver of block 784 from the optical sensor, and to perform any necessary amplification on the electrical signals. The electrical signals are indicative of detected light variations, which are in turn indicated by the optical signal received at the receiver of block 784. The Radio Frequency transmitter transmits electromagnetic radiation indicative of the output of the optical to audio conversion circuitry in wireless fashion from antenna 785. This wireless transmission method is only one of many possible techniques for making available the device's output. In variations on the FIG. 25 embodiment of the inventive device, the output of the device's electronics package (or more generally, the output of the device's acoustic transducer) can be transmitted from the device using any method of signal transmission or otherwise output from the device in any manner.

For simplicity, FIG. 25 does not show a power source or on-off switch, but such elements would typically be included in the FIG. 25 device.

Diaphragm assembly 767-788 includes thin, relatively stiff central diaphragm membrane 771, rim portion 768, and flexible annular convolutions 768, 769 and 770, as well as extension cups 787 and 788. In operation of the FIG. 25 device, movement of diaphragm membrane 771 in sympathy with sounds of interest (e.g., body sounds) is indicated as modulations of the light output from the optical sensor (the transducer coil portion of fiber 774) which propagates to the optical sensor through fiber 774 from the transmitter in block 784 and from the optical sensor back to the receiver in block 784.

As shown in FIG. 25, extension cup 788 is molded from the approximate midpoint of annular convolutions 768 and 769, and extension cup 787 is molded from the approximate midpoint of annular convolutions 769 and 770. The design of FIG. 25 allows diaphragm membrane 771 to move (e.g., vibrate) with respect to mass 752 and mass 782, while mass 752 and mass 782 (held in the extension cups), diaphragm portion 771, and each other portion of the diaphragm assembly in contact with the relevant surface (e.g., the patient's skin) move freely with respect to housing 786. When device 772's distal face (the right face in FIG. 25) is placed against the relevant surface, diaphragm portion 771 and masses 752 and 782 freely float on the surface while body 786 and clamp ring 754 are isolated greatly from diaphragm portion 771 and masses 752 and 782, and thus from the device's acoustic transducer, by annular convolutions 768, 769, and 770.

Although the acoustic transducer of device 772 of FIG. 25 is typically an optical sensor through which optical radiation propagates during use, in variations on the embodiment of FIG. 25, the inventive device includes an acoustic transducer similar to the optical sensor described with reference to FIG. 25 except in that non-optical electromagnetic radiation (e.g., infrared or other non-visible electromagnetic radiation) that propagates therethrough is modulated by movement of a diaphragm in sympathy with body sounds (or other sounds) of interest that are incident on the diaphragm. In other variations on the embodiment of FIG. 25, the inventive device includes an acoustic transducer of another type.

Seventeenth Embodiment

A High Ambient Noise Rejecting Stethoscope or Sound Detection Device

Figure 26:
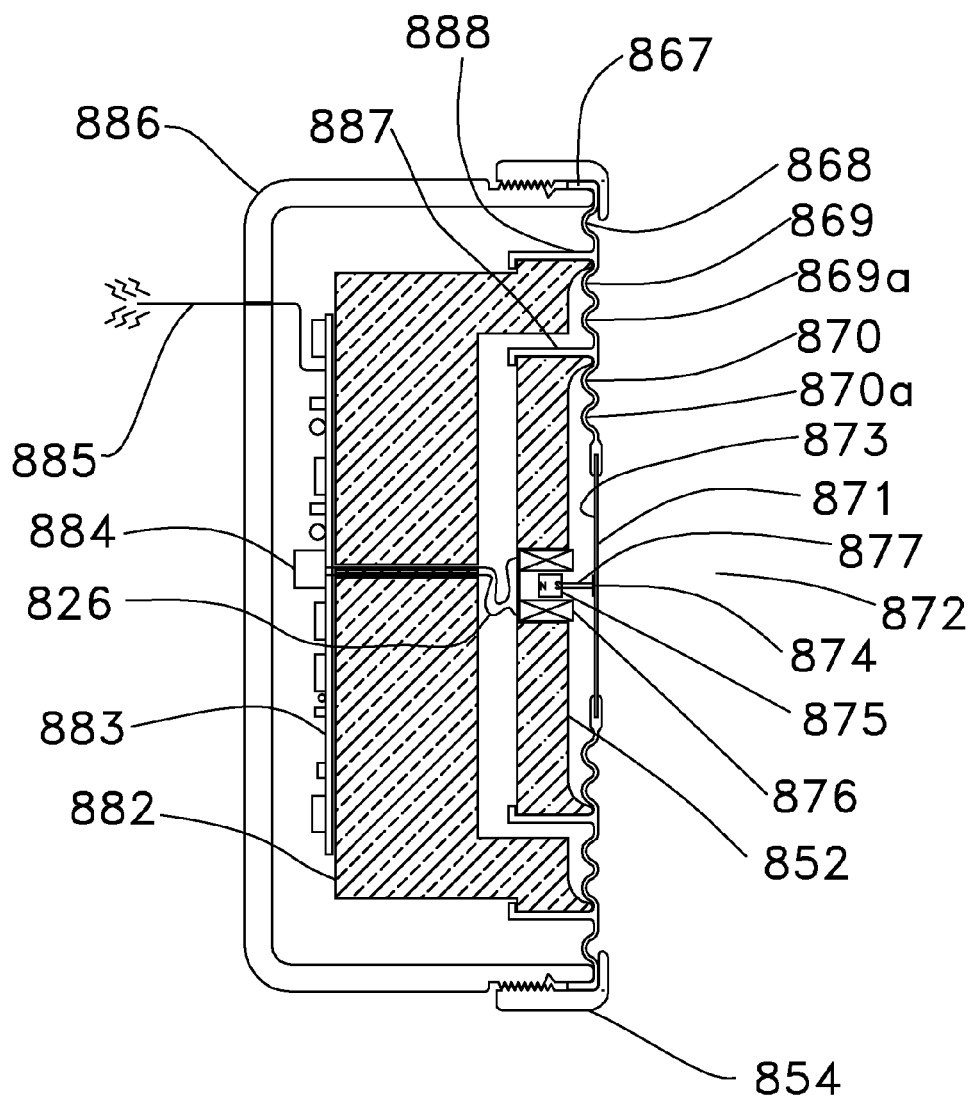
FIG. 26 is a side cross-sectional view of an embodiment of the inventive sound pickup device which can be used for many applications including as a stethoscope chest piece, and which includes two floating masses (852 and 882) and an inductive transducer. The inductive transducer converts sound of interest (e.g., body sounds) into an electromagnetic signal that is transmitted wirelessly via an antenna 885.

FIG. 26 is a half section of an embodiment of an electronic, high ambient noise rejecting, sound detection device (872) which can function as a stethoscope chest piece and is built according to the present invention. Device 872 comprises inductive sensor 876 which is mounted to floating mass 852 and biased against (or mounted to) inner face 873 of diaphragm membrane 871 so as to remain in contact with face 873 as shown in FIG. 26 during operation. Shaft 877 is mounted (typically, bonded) to face 873. More specifically, the inductive sensor includes coil 876 (typically a miniature multi turn coil of wire) mounted to mass 852, and small permanent magnet 875 attached to shaft 877. Shaft 877 positions magnet 875 inside coil 876 so that magnet 875 is free to translate linearly (parallel to the longitudinal axis of coil 876) relative to the coil. In use, shaft 877 and magnet 875 move together as a rigid unit in sympathy with membrane 871 as membrane 871 moves in sympathy with acoustic waves of interest (e.g., body sounds to be detected), and the inductive sensor asserts an electrical signal (indicative of the acoustic waves) from coil 876 to wires 826.

The FIG. 26 assembly includes two floating masses: floating mass 852 and floating mass 882. Each floating mass is mounted to specially molded diaphragm assembly 867-888 in housing 886 (which functions as a chest piece housing when the FIG. 26 assembly functions as a stethoscope chest piece). As shown, floating mass 852 is mounted to diaphragm assembly 867-888 in the sense that it is held in cup-like extension molding 887 of the diaphragm assembly (which extends in the proximal direction as shown from the rest of diaphragm assembly) by pressure of fit. As shown, floating mass 882 (which is preferably larger than mass 852) is mounted to the diaphragm assembly in the sense that it is held in cup-like extension molding 888 of the diaphragm assembly (which extends in the proximal direction as shown from the rest of diaphragm assembly) by pressure of fit. Alternatively, one or both of mass 852 and mass 882 is mounted to the diaphragm assembly by glue or other mounting means.

Mounted on mass 882 is an electronic package 883 which performs all necessary functions to process the electrical signals asserted via wires 826 from the inductive sensor. Components of electronic package 883 include amplifier/equalizer 884 (coupled to wires 826 to receive the electrical output of coil 876), antenna 885, a Radio Frequency transmitter coupled to antenna 885, and optionally also a sound processor. Amplifier/equalizer 884 is configured to amplify the electrical signals from the inductive sensor, which are indicative of detected acoustic waves. Preferably, amplifier/equalizer 884 is a device capable of detecting minute changes in voltage induced by magnet 875 into inductive sensor coil 876 in response to movement of the diaphragm 871 during sound detection.

The Radio Frequency transmitter transmits electromagnetic radiation indicative of the amplified electrical signals in wireless fashion from antenna 885. This wireless transmission method is only one of many possible techniques for making available the device's output. In variations on the FIG. 26 embodiment of the inventive device, the output of the device's electronics package (or more generally, the output of the device's acoustic transducer) can be transmitted from the device using any method of signal transmission or otherwise output from the device in any manner.

For simplicity, FIG. 26 does not show a power source or on-off switch, but such elements would typically be included in the FIG. 26 device.

Diaphragm assembly 867-888 includes thin, relatively stiff central diaphragm membrane 871, rim portion 867, and flexible annular convolutions 868, 869, 869*a*, 870, and 870*a*, as well as extension cups 887 and 888. In operation of the FIG. 26 device, movement of diaphragm membrane 871 in sympathy with sounds of interest (e.g., body sounds) is indicated as modulations of the electrical signal output from coil 876.

As shown in FIG. 26, extension cup 888 is molded from the approximate midpoint of annular convolutions 868 and 869, and extension cup 887 is molded from the approximate midpoint of annular convolutions 869a and 870. The design of FIG. 26 allows diaphragm membrane 871 to move (e.g., vibrate) with respect to mass 852 and mass 882, while mass 852 and mass 882 (held in the extension cups), diaphragm portion 871, and each other portion of the diaphragm assembly in contact with the relevant surface (e.g., the patient's skin) move freely with respect to housing 886. When device 872's distal face (the right face in FIG. 26) is placed against the relevant surface, diaphragm portion 871 and masses 852 and 882 freely float on the surface while body 886 and clamp ring 854 are isolated greatly from diaphragm portion 871 and masses 852 and 882, and thus from the device's acoustic transducer, by the annular convolutions 868, 869, 869a, 870, and 870a.

Although the acoustic transducer of device 772 of FIG. 26 is an inductive sensor, in variations on the FIG. 26 embodiment, the inventive device includes an acoustic transducer of another type.

Although the diaphragm assembly of FIG. 26 has five flexible annular convolutions 868, 869, 869a, 870, 870a, more or less than five can be present in variations on the diaphragm design shown in FIG. 26.

The materials available for the present invention are many. For example, typical embodiments of the housing of the inventive sound pickup device can be:
 a) Metal or metal alloy (e.g., aluminum, stainless steel, brass, bronze, and die cast metal);
 b) Plastic (e.g., PVC, acrylic, or ABS);
 c) Highly loaded acoustic energy absorbing plastic; and/or
 d) A plastic composite (e.g., plastic and a powdered metal compound, which is sometimes called a high gravity plastic).

The materials for typical embodiments of the diaphragm can be:
 a) Polyurethane resin or other advanced compounds;
 b) Various synthetic rubbers; and/or
 c) Highly loaded acoustic energy absorbing plastics.

The materials for typical embodiments of the floating mass can be:
 a) Metal or metal alloy (e.g., lead, bismuth-tin, brass, bronze, or die cast metal);
 b) Plastic composites (e.g., plastic and a powdered metal compound, which is sometimes called a high gravity plastic);
 c) Metal powders or micro balls held in an appropriate thin wall container shaped as desired; or
 d) Highly loaded acoustic energy absorbing plastics.

Preferred embodiments of the present invention perform in a manner that provides a significant improvement over the performance achievable by conventional electronic stethoscopes and sound detection devices. Great care was taken in its development with the concomitant time and energy to make it as practical and easy to use as a standard acoustic unit. In typical embodiments of the inventive device, the floating ballast mass (to which the diaphragm is mounted) is key to improved signal to noise performance achieved by such embodiments.

Table 1 (set forth below) is a tabulation of comparative test results of various stethoscopes which illustrates the signal to noise performance advantage of two embodiments of the invention over five commercially sold conventional stethoscopes:

TABLE 1

| Stethoscope Number | Stethoscope Description | S/N (in dB) w/Noise Reduct | S/N (in dB) w/o Noise Reduct |
|---|---|---|---|
| 1 | FIG. 3a-3d embodiment of invention | na | 36 |
| 2 | FIG. 8 embodiment of invention | na | 31 |
| 3 | Thinklabs Ds32A | 22 | 7 |
| 4 | Electromax 04-1060 | na | 0 |
| 5 | DGR Echo | 17 | na |
| 6 | Welch Allyn Master Elite | 24 | na |
| 7 | Littmann 3000 | 22 | na |

In Table 1, the phrase "S/N (in dB) with Noise Reduct" denotes measured signal to noise ratio (in units of Decibels) during operation of the relevant stethoscope with noise reduction circuitry, and "S/N (in dB) without Noise Reduct" denotes measured signal to noise ratio (in units of Decibels) during operation of the relevant stethoscope without noise reduction circuitry (or with deactivated or disabled noise reduction circuitry).

Table 1 was generated by comparing five commercially available conventional units with two embodiments of the inventive stethoscope described with reference to FIGS. 3a-3d and FIG. 8, respectively. The tested units were:
 1. the embodiment of the present invention described with reference to FIGS. 3a-3d;
 2. the embodiment of the present invention described with reference to FIG. 8, which differs from that of FIGS. 3a-3d only in that the chest piece of FIG. 8 (with a silicone rubber sheath 95) replaces the chest piece of FIGS. 3a-3d;
 3. Thinklabs' Digital Electronic Stethoscope Rhythm Model ds32A;
 4. Labtron's ElectroMax Stethoscope Model 04-1060;
 5. Doctors Research Group, Inc. "Echo Amplified" Stethoscope;
 6. Welch Allyn's Master Elite™ Electronic Stethoscope; and
 7. Littmann Electronic Stethoscope Model 3000.

The test results indicate that both tested embodiments of the present invention substantially outperformed the commercial units in the three most important categories of
 i) Signal to noise;
 ii) Finger noise; and
 iii) Signal definition and sharpness.

Each device rested on the top surface of a sound source while being tested. To measure the signal to noise ratios set forth in Table 1, the signal detected was 900 Hz vibration of the sound source, and the noise source was an amplified loudspeaker emitting 900 Hz sound waves (the 900 Hz noise propagated through the room from the loudspeaker to each device being tested).

Table 1 speaks for itself. Even without noise reduction, the signal to noise ratios measured for both embodiments of the present invention rank above the signal to noise ratios measured for all five other models tested.

The results for finger noise and signal definition are not easy to measure quantitatively because there is no agreed upon definition for these two quantities, and instead subjective observations thereof are reported herein. During the tests, all five commercial models produced varying degrees of finger noise. The Thinklabs unit (#3 in Table 1) offers variable gain and its instruction manual (which does not come with the unit but must be downloaded from the manufacturer's web site) points out that the user should restrict the gain to make sure that finger noise is acceptable. However both tested embodiments of the present invention (and especially the shielded FIG. 8 embodiment) produced so little finger noise that they operated usefully with more gain than did the commercial models.

The five commercial units attempt to minimize noise pickup by severely restricting the frequency bandwidth and/or by using electronic noise reduction. As a result of this, the heart sounds they generate are heard uniformly as a "dull thud" with little definition. The two tested embodiments of the present invention on the other hand, offer excellent signal definition through the use of circuitry that allows the user to hear the higher frequency colors of all the chest cavity sounds.

The tested embodiments of the present invention thus proved to be superior to all five commercial models tested by many Decibels when quantitative measurements (of signal to noise ratio) were available and by clearly observable differences when it was necessary to rely on subjective evaluation. The tested embodiments of the present invention achieve a better signal to noise without electronic noise reduction than any of the tested commercial units, regardless of whether the commercial units operated with or without electronic noise reduction. This demonstrates clearly the superiority of the present invention.

Although the descriptions above contain many specificities these should not be construed as limiting the scope of the invention but as merely providing illustrations of some of the presently preferred embodiments of this invention. The scope of the invention should be determined by the appended claims and their legal equivalents rather than by the examples provided.

What is claimed is:

1. An active sound detection device, including:
    a diaphragm;
    at least one rigid floating mass mounted to the diaphragm at at least one coupling point of the diaphragm such that when the diaphragm moves, the at least one floating mass moves in phase with and in sympathy with the diaphragm at each said coupling point; and
    an acoustic transducer mounted to at least one said floating mass.

2. The device of claim 1, wherein the at least one floating mass includes a first floating mass mounted to the diaphragm and a second floating mass mounted to the diaphragm.

3. The device of claim 2, wherein the acoustic transducer is mounted to the first floating mass but not to the second floating mass.

4. An active sound detection device, including:
    a diaphragm;
    at least one floating mass mounted to the diaphragm, wherein the at least one floating mass includes a first floating mass mounted to the diaphragm and a second floating mass mounted to the diaphragm; and
    an acoustic transducer mounted to at least one said floating mass, wherein the diaphragm has a first annular region and a second annular region concentric with the first annular region, said device also including:
    a housing to which the diaphragm is mounted, wherein the first floating mass is mounted the first annular region of said diaphragm with freedom to move relative to the housing in sympathy with movement of said first annular region, and the second floating mass is mounted to the second annular region of said diaphragm with freedom to move relative to the housing in sympathy with movement of said second annular region.

5. The device of claim 4, wherein the acoustic transducer is an optical transducer including an optical fiber having a transducer coil portion mounted to the first floating mass and coupled to a distal face of the diaphragm so as to remain in contact with the distal face during operation of the device.

6. The device of claim 4, wherein the acoustic transducer is an inductive transducer including a coil mounted to the first floating mass and a magnet mounted to the diaphragm.

7. The device of claim 1, wherein the floating mass is mounted to the diaphragm at the at least one coupling point of the diaphragm such that the floating mass and each said coupling point of the diaphragm move in sympathy with acoustic waves to be detected that impinge on the diaphragm, and wherein the floating mass, the diaphragm, and the acoustic transducer are configured such that while the floating mass and each said coupling point so move, the acoustic transducer rides with the floating mass and the floating mass stabilizes both the acoustic transducer and the diaphragm.

8. The device of claim 1, also including a housing to which the diaphragm is mounted, wherein the floating mass is mounted to the diaphragm at the at least one coupling point of said diaphragm with freedom to move relative to the housing in sympathy with movement of the coupling point.

9. The device of claim 8, wherein the diaphragm includes:
    a rim portion mounted to the housing;
    a central membrane; and
    an isolating portion between the rim portion and each said coupling point of the diaphragm, wherein the isolating portion is configured to prevent or reduce transmission of acoustic surface waves through said isolating portion from the rim portion to each said coupling point.

10. The device of claim 9, wherein the isolating portion includes at least one annular convolution of the diaphragm.

11. The device of claim 9, wherein the isolating portion consists of an annular convolution of the diaphragm.

12. The device of claim 9, wherein the diaphragm also includes:
    a second isolating portion between the membrane and each said coupling point of the diaphragm, wherein the second isolating portion is configured to prevent or reduce transmission of acoustic surface waves through said second isolating portion from the membrane to each said coupling point.

13. The device of claim 9, wherein said device is a stethoscope, the membrane is configured to be placed in contact with skin of a patient during operation of the stethoscope to detect body sounds, and the housing is a stethoscope chest piece housing.

14. The device of claim 8, wherein the diaphragm includes:
    a rim portion mounted to the housing;
    a central membrane; and
    an isolating portion between the rim portion and each said coupling point of the diaphragm, wherein the isolating portion is configured to prevent or reduce transmission of acoustic waves through said isolating portion from the housing to each said coupling point.

15. The device of claim 1, wherein said device is a stethoscope, at least a portion of the diaphragm is configured to be placed in contact with skin of a patient during operation of the stethoscope to detect body sounds.

16. The device of claim 1, wherein the acoustic transducer is a microphone.

17. The device of claim 1, wherein the acoustic transducer is an optical sound transducer.

18. The device of claim 1, wherein the acoustic transducer is a capacitive sound transducer.

19. The device of claim 1, wherein the acoustic transducer is an inductive sound transducer.

20. The device of claim 19, wherein the inductive transducer includes a coil mounted to the floating mass and a magnet mounted to the diaphragm.

21. The device of claim 1, wherein said device is a stethoscope and also includes:
   a chest piece including the floating mass, the acoustic transducer, and a housing, wherein the diaphragm is mounted to the housing, and the floating mass is mounted to the diaphragm at the at least one coupling point of said diaphragm with freedom to move relative to the housing in sympathy with movement of the coupling point; and
   a headset coupled to the chest piece, wherein the headset includes at least one output transducer coupled and configured to produce output sound in response to output of the acoustic transducer.

22. The device of claim 21, wherein the acoustic transducer is configured to generate at least one electrical signal in response to body sound causing movement of the diaphragm, and the output transducer is coupled and configured to convert at least one said electrical signal into the output sound.

23. The device of claim 21, also including:
   output transducer driving circuitry coupled and configured to generate at least one electrical signal in response to output of the acoustic transducer, and wherein the output transducer is coupled and configured to convert at least one said electrical signal into the output sound.

24. The device of claim 23, wherein the acoustic transducer is an optical sound transducer, and the output of said acoustic transducer is an optical signal.

25. The device of claim 1, also including a housing to which the diaphragm is mounted, wherein the floating mass is mounted to the diaphragm at the at least one coupling point of said diaphragm with freedom to move relative to the housing in sympathy with movement of the coupling point, and wherein the device defines a resonant chamber that provides chamber resonance to augment sounds to be detected by the device.

26. The device of claim 1, also including:
   a housing to which the diaphragm is mounted, wherein the floating mass is mounted to the diaphragm at the at least one coupling point of said diaphragm with freedom to move relative to the housing in sympathy with movement of the coupling point; and
   acoustic damping material on at least one element of the device, for damping vibration of each said element.

27. The device of claim 26, wherein the acoustic damping material coats at least a portion of the housing.

28. The device of claim 26, wherein said device is a stethoscope, at least a portion of the diaphragm is configured to be placed in contact with skin of a patient during operation of the stethoscope to detect body sounds, and the acoustic damping material is coated so as to prevent ambient noise from reaching an interface between the skin of the patient and a sensitive portion of the diaphragm.

29. The device of claim 26, wherein the acoustic damping material coats at least a portion of the floating mass.

30. The device of claim 26, also including:
   an electronic assembly coupled to the acoustic transducer, wherein the acoustic damping material coats at least a portion of the electronic assembly.

31. The device of claim 30, wherein the electronic assembly is mounted to the floating mass.

32. The device of claim 30, wherein the electronic assembly is mounted to the housing, and the acoustic damping material also coats at least a portion of the floating mass.

33. The device of claim 30, wherein the acoustic transducer is an optical transducer including at least one optical fiber section mounted to the floating mass, and wherein said device is a non-powered device that is constructed of non-magnetic and non-metallic materials.

34. The device of claim 33, wherein said device is configured for use as a stethoscope chest piece in presence of an intense magnetic field, said device also including a chest piece housing to which the diaphragm is mounted, wherein the floating mass is mounted to the diaphragm at the at least one coupling point of said diaphragm with freedom to move relative to the housing in sympathy with movement of the coupling point.

35. The device of claim 33, wherein the optical transducer includes a transducer coil portion mounted to the floating mass and coupled to a distal face of the diaphragm so as to remain in contact with the distal face during operation of the device.

36. The device of claim 33, wherein the optical transducer includes a first optical fiber section mounted to the floating mass and orientated for directing optical radiation to a distal face of the diaphragm, and a second optical fiber section mounted to the floating mass in an orientation for receiving optical radiation that has reflected from the distal face after propagating to said distal face from the first optical fiber section.

37. The device of claim 1, wherein the acoustic transducer is an optical transducer configured to convert sound into optical waves, said device also including:
   an antenna; and
   an electronic assembly coupled and configured to convert the optical waves into an electromagnetic signal and to transmit the electromagnetic signal wirelessly from the antenna.

38. The device of claim 1, wherein the acoustic transducer is configured to convert sound into an electrical signal, said device also including:
   an antenna; and
   an electronic assembly coupled and configured to convert the electrical signal from the acoustic transducer into an electromagnetic signal and to transmit the electromagnetic signal wirelessly from the antenna.

39. An active stethoscope, including:
   a chest piece housing;
   a head piece;
   a stethoscope tube assembly coupled between the housing and the head piece;
   a diaphragm mounted to the housing;
   at least one rigid floating mass mounted to the diaphragm at at least one coupling point of the diaphragm such that when the diaphragm moves, the at least one floating mass moves in phase with and in sympathy with the diaphragm at each said coupling point;

an acoustic transducer, mounted to the floating mass and configured to generate at least one transducer output signal in response to body sound causing movement of the diaphragm; and at least one output transducer is coupled and configured to receive at least one said transducer output signal and to convert the at least one said transducer output signal into output sound indicative of the body sound.

40. The stethoscope of claim 39, wherein the acoustic transducer is an acoustic to electrical transducer, said stethoscope also including:

amplifier circuitry including an input coupled to the acoustic to electrical transducer and an output coupled to the output transducer.

41. The stethoscope of claim 39, wherein the floating mass is mounted to the diaphragm at the at least one coupling point of said diaphragm with freedom to move relative to the housing in sympathy with movement of the coupling point.

42. The stethoscope of claim 39, wherein the floating mass is mounted to the diaphragm at the at least one coupling point of the diaphragm such that the floating mass and each said coupling point of the diaphragm move in sympathy with said body sound, and wherein the floating mass, the diaphragm, and the acoustic transducer are configured such that while the floating mass and each said coupling point so move, the acoustic transducer rides with the floating mass and the floating mass stabilizes both the acoustic transducer and the diaphragm.

43. The stethoscope of claim 39, wherein said stethoscope defines a resonant chamber within the housing that provides chamber resonance to augment body sounds to be detected by said stethoscope.

44. An active stethoscope, including:
a chest piece housing;
a diaphragm mounted to the housing;
at least one rigid floating mass mounted to the diaphragm at at least one coupling point of the diaphragm such that when the diaphragm moves, the at least one floating mass moves in phase with and in sympathy with the diaphragm at each said coupling point; and
an acoustic transducer mounted to at least one said floating mass.

45. The stethoscope of claim 44, wherein the acoustic transducer is configured to generate at least one transducer output signal in response to body sound causing movement of the diaphragm, said stethoscope also including:
a head piece; and
a stethoscope tube assembly coupled between the housing and the head piece, wherein the head piece includes at least one output transducer coupled and configured to receive at least one said transducer output signal and to convert the at least one said transducer output signal into output sound indicative of the body sound.

46. The stethoscope of claim 44, wherein the at least one floating mass includes a first floating mass mounted to the diaphragm and a second floating mass mounted to the diaphragm, and the acoustic transducer is mounted to the first floating mass.

47. The stethoscope of claim 46, wherein the acoustic transducer is mounted to the first floating mass but not to the second floating mass.

48. An active stethoscope, including:
a chest piece housing;
a diaphragm mounted to the housing;
at least one floating mass mounted to the diaphragm; and
an acoustic transducer mounted to at least one said floating mass, wherein the at least one floating mass includes a first floating mass mounted to the diaphragm and a second floating mass mounted to the diaphragm, and the acoustic transducer is mounted to the first floating mass, and wherein the diaphragm has a first annular region and a second annular region concentric with the first annular region, the first floating mass is mounted the first annular region of said diaphragm with freedom to move relative to the housing in sympathy with movement of said first annular region, and the second floating mass is mounted to the second annular region of said diaphragm with freedom to move relative to the housing in sympathy with movement of said second annular region.

49. The stethoscope of claim 44, wherein the floating mass is mounted to the diaphragm at the at least one coupling point of the diaphragm such that the floating mass and each said coupling point of the diaphragm move in sympathy with body sound that impinges on the diaphragm, and wherein the floating mass, the diaphragm, and the acoustic transducer are configured such that while the floating mass and each said coupling point so move, the acoustic transducer rides with the floating mass and the floating mass stabilizes both the acoustic transducer and the diaphragm.

50. The stethoscope of claim 44, wherein the floating mass is mounted to the diaphragm at the at least one coupling point of said diaphragm with freedom to move relative to the housing in sympathy with movement of the coupling point.

51. The stethoscope of claim 50, wherein the diaphragm includes:
a rim portion mounted to the housing;
a central membrane; and
an isolating portion between the rim portion and each said coupling point of the diaphragm, wherein the isolating portion is configured to prevent or reduce transmission of acoustic surface waves through said isolating portion from the rim portion to each said coupling point.

52. The stethoscope of claim 51, wherein the isolating portion includes at least one annular convolution of the diaphragm.

53. The stethoscope of claim 51, wherein the diaphragm also includes:
a second isolating portion between the membrane and each said coupling point of the diaphragm, wherein the second isolating portion is configured to prevent or reduce transmission of acoustic surface waves through said second isolating portion from the membrane to each said coupling point.

54. The stethoscope of claim 50, wherein the diaphragm includes:
a rim portion mounted to the housing;
a central membrane; and
an isolating portion between the rim portion and each said coupling point of the diaphragm, wherein the isolating portion is configured to prevent or reduce transmission of acoustic waves through said isolating portion from the housing to each said coupling point.

55. The stethoscope of claim 44, wherein the acoustic transducer is a microphone.

56. The stethoscope of claim 44, wherein the acoustic transducer is an optical sound transducer.

57. The stethoscope of claim 44, wherein the acoustic transducer is a capacitive sound transducer.

58. The stethoscope of claim 44, wherein the acoustic transducer is an inductive sound transducer.

59. The stethoscope of claim 58, wherein the inductive transducer includes a coil mounted to the floating mass and a magnet mounted to the diaphragm.

60. The stethoscope of claim 44, also including:
acoustic damping material on at least one element of the stethoscope, for damping vibration of each said element.

61. The stethoscope of claim 60, wherein the acoustic damping material coats at least a portion of the housing.

62. The stethoscope of claim 60, wherein the acoustic damping material coats at least a portion of the floating mass.

63. The stethoscope of claim 62, also including:
an electronic assembly coupled to the acoustic transducer, wherein the acoustic damping material coats at least a portion of the electronic assembly.

64. The stethoscope of claim 44, wherein said stethoscope defines a resonant chamber within the housing that provides chamber resonance to augment body sounds to be detected by said stethoscope.

* * * * *